(12) United States Patent
Slepian

(10) Patent No.: US 10,226,552 B2
(45) Date of Patent: Mar. 12, 2019

(54) MATERIALS, SYSTEMS, DEVICES, AND METHODS FOR ENDOLUMINAL ELECTROPOLYMERIC PAVING AND SEALING

(71) Applicant: The Arizona Board of Regents on behalf of the University of Arizona, Tucson, AZ (US)

(72) Inventor: Marvin J. Slepian, Tucson, AZ (US)

(73) Assignee: Arizona Board of Regents on Behalf of the Unviersity of Arizona, Tucson, AZ (US)

( * ) Notice: Subject to any disclaimer, the term of this patent is extended or adjusted under 35 U.S.C. 154(b) by 424 days.

(21) Appl. No.: 14/781,843

(22) PCT Filed: Apr. 4, 2014

(86) PCT No.: PCT/US2014/033078
§ 371 (c)(1),
(2) Date: Oct. 1, 2015

(87) PCT Pub. No.: WO2014/165822
PCT Pub. Date: Oct. 9, 2014

(65) Prior Publication Data
US 2016/0051735 A1    Feb. 25, 2016

Related U.S. Application Data

(60) Provisional application No. 61/808,545, filed on Apr. 4, 2013.

(51) Int. Cl.
*A61L 31/16* (2006.01)
*A61L 31/14* (2006.01)
(Continued)

(52) U.S. Cl.
CPC ............ *A61L 31/16* (2013.01); *A61B 5/0031* (2013.01); *A61B 5/026* (2013.01); *A61B 5/0215* (2013.01);
(Continued)

(58) Field of Classification Search
CPC . A61N 1/37205; A61N 1/326; A61L 2400/06; A61L 31/16; A61L 31/148;
(Continued)

(56) References Cited

U.S. PATENT DOCUMENTS 2,675,619 A    4/1954  Cone
2,677,700 A    5/1954  Jackson
(Continued)

FOREIGN PATENT DOCUMENTS

EP    1847217        10/2007
EP    1847217 A2 *  10/2007  ........... A61B 5/0031

OTHER PUBLICATIONS

Albertsson, et al. "The mechanism of biodegradation of polyethylene", Polymer Degradation and Stability, 18:73-87 (1987).
(Continued)

*Primary Examiner* — Michael Carey
(74) *Attorney, Agent, or Firm* — Pabst Patent Group LLP

(57) ABSTRACT

Methods, materials, devices, and systems for electropolymeric paving and sealing (ePEPS) are provided. The methods include delivering paving materials to an interior surface of a blood vessel, tissue lumen or other hollow space, delivering electronic components to the surface, and forming a conformal device that contains the paving material and the integrated electronic components. Integrated electronic components can be homogenously or heterogeneously distributed in the material, such as on the top, middle, and/or bottom of the polymeric material. The devices are biocompatible, and preferably biodegradable or bioerodible. The
(Continued)

devices integrated electrical properties useful for sensing or detecting one or more analytes, signals or conditions, transmitting or generating a signal, or releasing a therapeutic, prophylactic or diagnostic agent. Optionally, the devices are smart devices that include feedback and logic means to respond to a change in local conditions.

17 Claims, 5 Drawing Sheets

(51) Int. Cl.
| | |
|---|---|
| *A61F 2/945* | (2013.01) |
| *A61B 5/00* | (2006.01) |
| *A61B 5/026* | (2006.01) |
| *A61B 5/07* | (2006.01) |
| *A61N 1/32* | (2006.01) |
| *A61N 1/372* | (2006.01) |
| *A61B 5/0215* | (2006.01) |
| *A61F 2/82* | (2013.01) |
| *A61L 31/04* | (2006.01) |
| *A61B 5/01* | (2006.01) |
| *A61B 5/11* | (2006.01) |
| *A61B 5/145* | (2006.01) |
| *A61B 8/06* | (2006.01) |
| *A61B 8/12* | (2006.01) |
| *A61B 8/08* | (2006.01) |

(52) U.S. Cl.
CPC .......... *A61B 5/076* (2013.01); *A61B 5/14539* (2013.01); *A61B 5/14546* (2013.01); *A61B 5/686* (2013.01); *A61F 2/82* (2013.01); *A61F 2/945* (2013.01); *A61L 31/04* (2013.01); *A61L 31/14* (2013.01); *A61L 31/148* (2013.01); *A61N 1/326* (2013.01); *A61N 1/37205* (2013.01); *A61B 5/01* (2013.01); *A61B 5/11* (2013.01); *A61B 5/14532* (2013.01); *A61B 8/06* (2013.01); *A61B 8/12* (2013.01); *A61B 8/488* (2013.01); *A61F 2210/0004* (2013.01); *A61F 2210/0085* (2013.01); *A61F 2250/0002* (2013.01); *A61F 2250/0043* (2013.01); *A61F 2250/0096* (2013.01); *A61L 2400/06* (2013.01)

(58) Field of Classification Search
CPC .. A61L 31/14; A61L 31/04; A61F 2250/0096; A61F 2250/0043; A61F 2250/0002; A61F 2250/0085; A61F 2250/0004; A61F 2/945; A61F 2/82; A61B 8/12; A61B 8/06; A61B 5/686; A61B 5/14546; A61B 5/14539; A61B 5/14532; A61B 5/11; A61B 5/076; A61B 5/026; A61B 5/0215; A61B 5/01; A61B 5/0031
USPC ....................................................... 600/301
See application file for complete search history.

(56) References Cited

U.S. PATENT DOCUMENTS

| | | | |
|---|---|---|---|
| 2,979,578 | A | 4/1961 | Cuttis |
| 3,036,118 | A | 5/1962 | Jackson |
| 3,535,307 | A | 10/1970 | Moss |
| 3,829,506 | A | 8/1974 | Schmolka |
| 3,868,956 | A | 3/1975 | Alfidi |
| 4,655,771 | A | 4/1987 | Wallsten |
| 4,938,763 | A | 7/1990 | Dunn |
| 5,213,580 | A | 5/1993 | Slepian |
| 5,328,471 | A | 7/1994 | Slepian |
| 5,575,815 | A | 11/1996 | Slepian |
| 5,634,946 | A * | 6/1997 | Slepian .................. A61F 2/062 128/898 |
| 5,674,287 | A | 10/1997 | Slepian |
| 5,749,922 | A | 5/1998 | Slepian |
| 5,807,258 | A | 9/1998 | Cimochowski |
| 5,843,156 | A | 12/1998 | Slepian |
| 5,863,024 | A | 1/1999 | Blind |
| 5,947,977 | A | 9/1999 | Slepian |
| 6,287,320 | B1 | 9/2001 | Slepian |
| 6,290,729 | B1 | 9/2001 | Slepian |
| 6,443,941 | B1 | 9/2002 | Slepian |
| 6,699,272 | B2 | 3/2004 | Slepian |
| 6,890,300 | B2 | 5/2005 | Lloyd |
| 8,336,387 | B2 | 12/2012 | Tai |
| 2010/0074934 | A1* | 3/2010 | Hunter ...................... A61F 2/16 424/422 |
| 2011/0237921 | A1 | 9/2011 | Askin, III et al. |
| 2012/0165759 | A1* | 6/2012 | Rogers ................ A61B 5/6867 604/264 |

OTHER PUBLICATIONS

Ashton, et al, "Polymeric endoaortic paving: Mechanical, thermoforming, and degradation properties of polycaprolactone/polyurethane blends for cardiovascular applications," Acta Biomaterialia, 7(1), 287-94, (2011).

Avichat, et al, "Recent Investigations of Plant Based Natural Gums, Mucilages and Resins in Novel Drug Delivery Systems", Ind. J. Pharm. Edu. Res., 24(a):86-99 (2010).

Dagdeviren, et al., "Conformal piezoelectric energy harvesting and storage from motions of the heart, lung, and diaphragm," PNAS, 111(5): 1927-32 (2014).

Herrmann, et al., "Electric-Field Triggered Controlled Release of Bioactive Volatiles from Imine-Based Liquid Crystalline Phases", Chemistry, 15:117-24 (2009).

Ricker, et al, "Corrosion of Metals",Evaluation of alternative In-Flight Fire Suppressants for Full-Scale Testing in Simulated Aircraft Engine Nacelles and Dry Bays. Section 7:669-728, edited by Grosshandler, et al. NIST (1994).

Slepian, et al., "Polymeric endoluminal paving. OA family of evolving methods for extending endoluminal therapeutics beyond stenting", Cardiology Clinics, 12(4):715-37 (1994).

International Search Report and Written Opinion for corresponding PCT Application PCT/US2014/033078 dated Jul. 10, 2014.

* cited by examiner

MATERIALS, SYSTEMS, DEVICES, AND METHODS FOR ENDOLUMINAL ELECTROPOLYMERIC PAVING AND SEALING

CROSS-REFERENCE TO RELATED APPLICATIONS

This application is a 371 application of International Application No. PCT/US2014/033078, which claims benefit and priority to U.S. Provisional Application Ser. No. 61/808,545, entitled "Materials, Systems, Devices, And Methods For Endoluminal Electropolymeric Paving And Sealing" to Marvin J. Slepian, filed Apr. 4, 2013, all of which are herein incorporated by reference.

FIELD OF THE INVENTION

This invention is generally in the field of paving and sealing the interior of organs or organ components with smart biodegradable implants.

BACKGROUND OF THE INVENTION

The human body contains a number of organs or organ components, both solid and tubular, having a hollow interior. Examples of hollow or tubular organs or organ components include the heart and arteries, the stomach, small and large intestines, bladder, lungs, etc. During the course of a lifetime, the function of these organ or organ components may change, including loss of function ("hypo-normal function"), enhancement of function ("hyper-" or "supra-normal function") or the attainment or "re-attainment" of normal functions. Hypo-normal function may develop due to atrophy, toxemia, environmental exposure, infection, inflammation, malignancy, injury, ischemia, malnutrition, radiation exposure, temperature alteration, infiltrative processes, fibrotic processes, calcification, lipid insulation, atherosclerosis, and/or physical and/or mechanical stressors. Hyper-normal function may develop due to hyperplasia, hypertrophy, different types of stimulation, including nutritional, metabolic, and/or supplement-stimulation, cellular infiltrative processes, exposure to a number of factors, including environment, radiation, hormones, temperature and/or pharmacological exposure, hyperemia, hyper- or super-fusion, malignancy, physical and/or mechanical stressors, and/or tissue implantation or transplantation.

An example of problems that occur in hollow organs can be seen looking at the coronary arteries. Coronary arteries, or arteries of the heart, perfuse the cardiac muscle with arterial blood. They also provide essential nutrients, removal of metabolic wastes, and gas exchange. These arteries are subject to relentless service demands for continuous blood flow throughout the life of the patient. Despite their critical life supporting function, coronary arteries are often subject to attack through several disease processes, the most notable being atherosclerosis (hardening of the arteries). Throughout the life of the patient, multiple factors contribute to the development of microscopic and/or macroscopic vascular lesions, known as plaques. The development of a plaque-lined vessel typically leads to an irregular inner vascular surface with a corresponding reduction of lumen cross-sectional area. The progressive reduction in cross-sectional area compromises flow through the vessel. In the case of the coronary arteries, the result is a reduction in blood flow to the cardiac muscle. This reduction in blood flow, coupled with a corresponding reduction in nutrient and oxygen supply, often results in clinical angina, unstable angina, myocardial infarction (heart attack), and death. The clinical consequences of the above process and its overall importance are evidenced by the fact that atherosclerotic coronary artery disease is a leading cause of death in the United States.

In 1987, a mechanical approach to combat atherosclerosis and restenosis was introduced. An intracoronary stent is a tubular device made of fine wire mesh, typically stainless steel. A stent of that type is disclosed in U.S. Pat. No. 4,655,771 to Hans Wallsten. The device can be radially compressed so as to be of low cross-sectional area. In this "low profile" condition, the mesh is placed in or on a catheter. The stent is then positioned at the site of the vascular region to be treated. Once in position, the wire mesh stent is released and allowed to expand to its desired cross-sectional area generally corresponding to the internal diameter of the vessel. Similar solid stents are also disclosed in U.S. Pat. No. 3,868,956 to Alfidi, et al. The metal stent functions as a permanent intra-vascular scaffold. By virtue of its material properties, the metal stent provides structural stability and direct mechanical support to endoluminal surfaces and the bulk of the vascular wall. Stents of the type described above are either balloon-expandable or resiliently self-expanding due to their helical "spring" geometry. Other stents have also been designed in recent years. Among these are stents formed from polymeric materials and stents formed from materials which exhibit shape memory.

The complications associated with permanent implants such as the coronary stents result from multiple factors including: (1) Issues related to the biocompatibility of the implant—local wall reaction, e.g. foreign body, inflammation, immune responses, wall tissue compression, specific material composition; (2) Alterations of blood flow resulting from the creation of flow disturbances due to protrusion of stent element in the blood flow field, as well as unusual geometries and topographies; (3) Underlying tissue, e.g. vessel wall issues and disease; and/or (4) Inherent design deficiencies in the stenting devices. The stent is a foreign object (i.e., not native to the body); it incites a thrombotic, inflammatory, local tissue reaction, and an immune response. This may cause cell activation, migration and proliferation to rapidly occur over the stent—termed "neointimal thickening" or "hyperplasia". In addition, there is a strong tendency for clots to form at the site where the stent damages the arterial wall. The size and/or structure of the stent may give rise to mechanical stability problems. Recent studies measuring the relative radial compressive stiffness of known wire stents, as compared to physiologically pressurized arteries, have found the stents to be much stiffer than biological tissue. These studies lend support to the concept of poor mechanical biocompatibility of many currently available stents. The permanent placement of a non-retrievable, non-degradable, foreign body in a vessel to combat restenosis, which is predominately limited to the six-month time period post-angioplasty, is another major drawback of coronary stenting, i.e., a temporal mismatch. Furthermore, typically the coronary stent is a purely structural element; it is not responsive and does not monitor changes in arterial function, i.e. does not monitor blood flow rates and/or the presence of an immune response to the stent.

It is therefore an object of this invention to provide materials and/or methods for forming smart biomedical implants on endoluminal surfaces without the need for invasive medical procedures.

It is a further object of this invention to provide improved materials and/or methods for forming smart biomedical implants on endoluminal surfaces that are biodegradable over the useful lifetime of the implant.

It is a further object of this invention to provide improved smart biomedical implants and systems for forming smart biomedical implants that are biodegradable in a controlled manner.

It is a further object of this inventions to provide improved materials and/or methods for forming smart biomedical implants on endoluminal surfaces that have integrated electronic devices that can locally monitor and/or modify the function of an organ or organ component.

SUMMARY OF THE INVENTION

Methods, materials, devices, and systems for electropolymeric paving have been developed and are described herein.

The methods include transporting or conveying materials to be placed on or affixed to a surface (the endoluminal surface) of a tissue, and deploying these materials to form a conformal endoluminal device.

The device includes a biocompatible implantable degradable polymeric material having integrated electrical properties useful for sensing or detecting one or more analytes, signals or conditions, transmitting or generating a signal, or releasing a therapeutic, prophylactic or diagnostic agent. In a preferred embodiment, the polymeric material is in a fluent state and is converted to a less fluent state when implanted, one or more conditions or stimuli, such as for example, by a change in temperature, electrical current, ultrasound, polymerization, and/or interaction with biological fluid. The polymeric material may include monomer or partially polymerized prepolymer that is polymerizable at the time of implantation. The degradable polymeric material degrades by hydrolysis, oxidation, enzymatic degradation, reductive mechanisms, Norrish type I or type II ester formation, or corrosion. The device may include integrated electrical or mechanical elements. Examples of integrated electrical or mechanical elements, but are not limited to, sensors, actuators, power storage, and power generation means. The polymeric material may be electrically conductive, an insulator, semiconductor, dielectric, or store energy. The integrated electrical or mechanical elements can be homogenously or heterogeneously distributed in the polymeric material, and are located on the top, middle or bottom of the polymeric material, or are in a combination of these locations. The device may further include a battery or other means for transmitting energy from an external source, such as radiofrequency, or magnetic resonators.

The device can be in the form of preformed shapes, including but not limited to, dots, spots, spirals, meshes, tubular constructs, materials that are continuous or discontinuous. The device can be applied as part of, or by means of, a stent or a continuous, perforated, or helical sleeve. The device can perform as, or include, one or more means for sensing flow, pressure, change in mass, pH a chemical analyte or adherent infiltrative cells or organisms, in a lumen or diagnostically or therapeutically created lumen or tissue space, detecting materials or signals related to restenosis, thrombosis, inflammation and infection or other processes, as well as general functional monitoring. The device adheres to the site of implantation. For example the polymeric material may adhere to the tissue. Alternatively or additionally, the device may include one or more components to mechanically adherent to the tissue. In one embodiment, the device includes one or more therapeutic, prophylactic or diagnostic agent(s) that are released after implantation, cells or other biological agents. In one embodiment, the device is used to kill infectious agents, tumor cells, or to sterilize a region or cells at the site of implantation.

The device is implanted or administered within a lumen. This is referred to as "electropolymeric paving". The lumen may be a blood vessel, such as the coronary, carotid, femoral, iliac, renal, vertebral, mesenteric, uterine, prostate arteries or veins, or intratumoral arteries. Alternatively, the lumen may be a tube such as bile ducts, fallopian tubes, ureter, urethra, trachea, bronchi, lacrimal duct or other ducts, the auditory canal or other canals or body cavity like the peritoneum, the thoracic cavity, the oral cavity, the rectal cavity, or the vaginal or uterine cavity. The device may also be implanted in created lumens or tissue spaces, resulting from disease processes, trauma, surgery, minimally invasive or percutaneous interventions. The device may be implanted within the lumen wall or between layers of the lumen wall, or on the tissue side of the lumen, for example, endolumenally or ectolumenally.

The paving material may be converted to a less fluent state. The paving material may be administered in conjunction with a deployed device such as a stent, graft, catheter, fistula, occlusion device, cavity filling device, tissue expander, barrier device, pacemaker, defibrillator, VAD, artificial heart, insulin pump or nerve stimulator. The paving material can be administered by spraying, brushing, rolling, or other application means or as a flowable liquid, and the liquid solidified by application of light, temperature change, by an electrical current, ultrasound, radiation, polymerization, or interaction with biological fluid. Alternatively, the paving material may be implanted using a catheter or trocar, or surgically.

BRIEF DESCRIPTION OF THE DRAWINGS

FIG. 9A depicts a paving layer with electronics distributed on top (connected); FIG. 9B depicts a paving layer with electronics on top though embedded, flush but communication to lumen; FIG. 9C depicts a paving layer with electronics within layer; FIG. 9D depicts a paving layer with electronics on top, within or on the bottom of the layer; FIG. 9E depicts a paving layer with electronics on top and within the layer; FIG. 9F depicts a paving layer with electronics distributed through multiple layers of the device (the electronics may be connected, although they are illustrated as single elements); and FIG.

9G depicts a paving layer with electronics distributed through and on top/bottom (i.e., ad and abluminal surfaces of device).

Figure 10A:
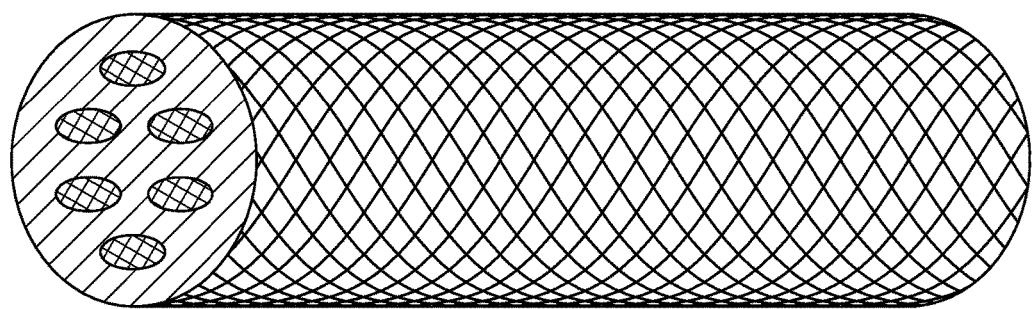
Figure 10B:
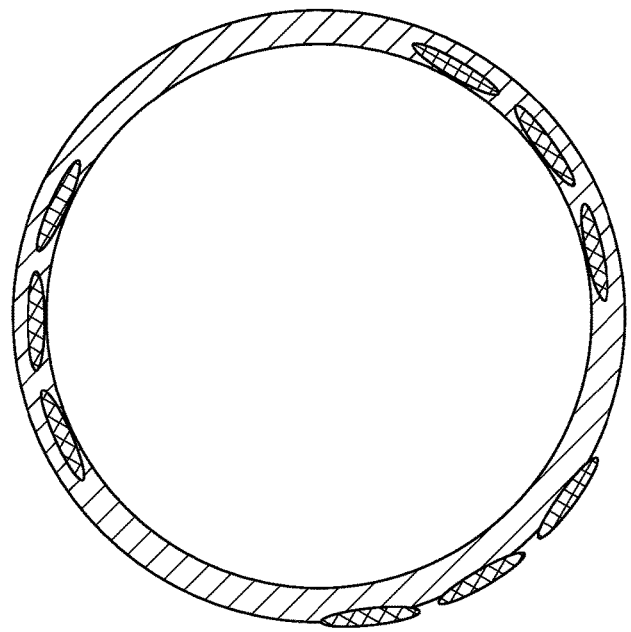
Figure 10C:
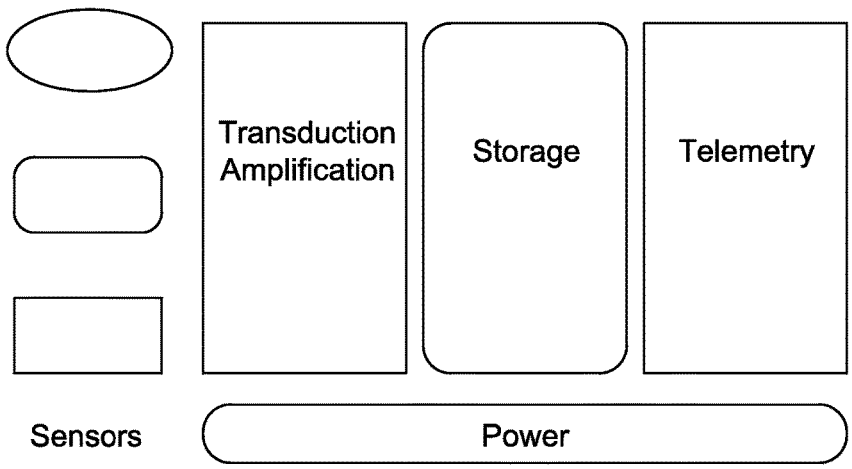

FIG. 10A-C are illustrations of a smart bioelectric paving device containing one or more polymer paving layers; a modular micro "motherboard"; and a microchip/microcircuit. FIG. 10A provides a side view of the device; FIG. 10B provides a cross-sectional view of the device, showing the paving layer and the electronic components; FIG. 10C depicts an exemplary micro motherboard.

Figure 11:
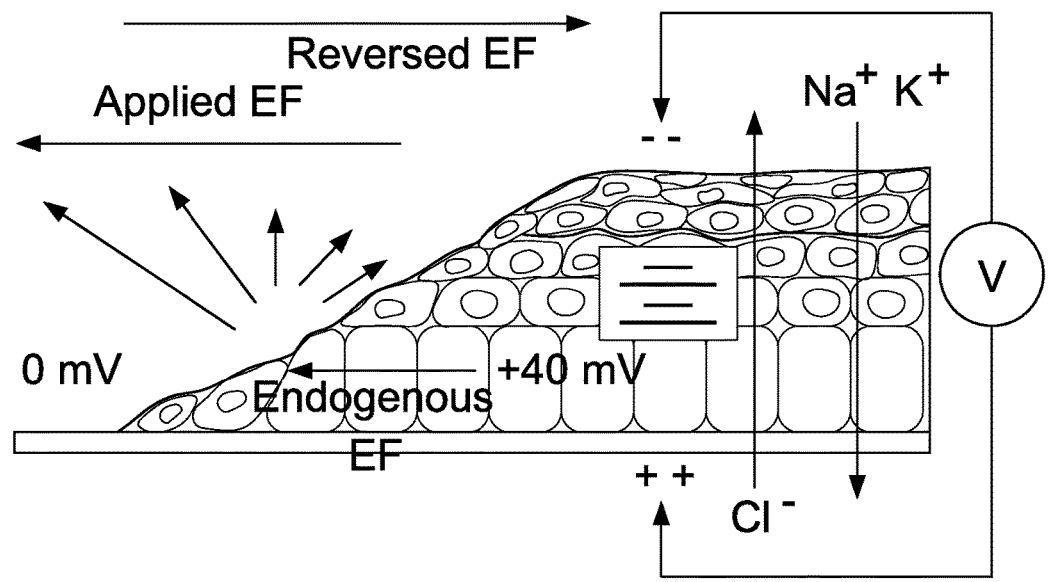

FIG. 11 is an illustration depicting how the use of a smart bioelectric paving device can produce an electric field (EF) that is effective to either inhibit or enhance (stimulate) cell growth. As depicted in FIG. 11, cells migrate to the anode (−) and are repelled by the cathode (+).

DETAILED DESCRIPTION OF THE INVENTION

I. Definitions

The terms "actuating element" and "actuator", as used interchangeably herein, refer to a device component useful for interacting with, stimulating, controlling, or otherwise affecting an external structure, material or fluid, for example a biological tissue. Useful actuating elements include, but are not limited to, electrode elements, electromagnetic radiation emitting elements, light emitting diodes, lasers and heating elements. Actuating elements include electrodes for providing a voltage or current to a tissue. Actuating elements include sources of electromagnetic radiation for providing electromagnetic radiation to a tissue. Actuating elements include ablation sources for ablating tissue. Actuating elements include thermal sources for heating tissue. Actuating elements include displacement sources for displacing or otherwise moving a tissue.

The term "barrier layer", as used herein, refers to a device component spatially separating two or more other device components or spatially separating a device component from a structure, material or fluid external to the device. In one embodiment, a barrier layer encapsulates one or more device components. In embodiments, a barrier layer separates one or more device components from an aqueous solution, a biological tissue and/or a biological environment. In some embodiments, a barrier layer is a passive device component. In some embodiments, a barrier layer is a functional, but non-active, device component. In a specific embodiment, a barrier layer is a moisture barrier. As used herein, the term "moisture barrier" refers to a barrier layer which provides protection to other device components from bodily fluids, ionic solutions, water or other solvents. In one embodiment, a moisture barrier provides protection to an external structure, material or fluid, for example, by preventing leakage current from escaping an encapsulated device component and reaching the external structure, material or fluid. In a specific embodiment, a barrier layer is a thermal barrier. As used herein, the term "thermal barrier" refers to a barrier layer which acts as a thermal insulator, preventing, reducing or otherwise limiting transferring heat from one device component to another or from a device component to an external structure, fluid or material. Useful thermal barriers include those comprising materials having a thermal conductivity of 0.3 W/m-K or less, such as selected over the range of 0.001 to 0.3 W/m-K. In some embodiments, a thermal barrier can have active cooling components, such as components known in the art of thermal management, such as thermoelectric cooling devices and systems. Thermal barriers also include those barriers comprising thermal management structures, such as structures useful for transporting heat away from a portion of a device or tissue; in these and other embodiments, a thermal barrier can be a thermally conductive material, for example material having a high thermal conductivity, such as a thermal conductivity characteristic of a metal.

The terms "bendable" and "flexible", as used interchangeably herein, refer to the ability of a material, structure, device or device component to be deformed into a curved or bent shape without undergoing a transformation that introduces significant strain, such as strain characterizing the failure point of a material, structure, device or device component. In some embodiments, a flexible material, structure, device or device component may be deformed into a curved shape without introducing strain larger than or equal to 5%, for some embodiments larger than or equal to 1%, and for yet other embodiments larger than or equal to 0.5% in strain-sensitive regions. A used herein, some, but not necessarily all, flexible structures are also stretchable. A variety of properties provide flexible structures (e.g., device components), including materials properties such as a low modulus, bending stiffness and flexural rigidity; physical dimensions such as small average thickness (e.g., less than 100 microns, optionally less than 10 microns and optionally less than 1 micron) and device geometries such as thin film and mesh geometries. In this description, a "bent configuration" refers to a structure having a curved conformation resulting from applying a force. Bent structures may have one or more folded regions, convex regions, concave regions, and any combinations thereof. Useful bent structures, for example, may be in a coiled conformation, a wrinkled conformation, a buckled conformation and/or a wavy (i.e., wave-shaped) configuration. Bent structures, such as stretchable bent interconnects, may be bonded to a flexible substrate, such as a polymer and/or elastic substrate, in a conformation wherein the bent structure is under strain. In some embodiments, the bent structure, such as a bent ribbon structure, is under a strain equal to or less than 30%, optionally a strain equal to or less than 10%, optionally a strain equal to or less than 5% and optionally a strain equal to or less than 1% in embodiments preferred for some applications. In some embodiments, the bent structure, such as a bent ribbon structure, is under a strain selected from the range of 0.5% to 30%, optionally a strain selected from the range of 0.5% to 10%, and optionally a strain selected from the range of 0.5% to 5%. Alternatively, the stretchable bent interconnects may be bonded to a substrate that is a substrate of a device component, including a substrate that is itself not flexible, The substrate itself may be planar, substantially planar, curved, have sharp edges, or any combination thereof. Stretchable bent interconnects are available for transferring to any one or more of these complex substrate surface shapes.

The term "bending stiffness", as used herein, is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

The terms "biocompatible" and "biologically compatible", as used interchangeably herein, refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

The term "biodegradable", as used herein, means that the material, structure, device, or device component degrades or breaks down into its component subunits, or digestion products, e.g., by a biochemical process, of the material into smaller (e.g., non-polymeric) subunits. Biodegradable materials, structures, devices, or device components are also be referred to as "transient." In some embodiments, a biodegradable material, structure, device, or device component degrades into $CO_2$, $H_2O$, and other biomass materials. In some embodiments, the degradation occurs over a period less than 30 days, less than 60 days, less than 90 days, less than 120 days, less than 180 days, less than 1 year. In some embodiments the degradation occurs over a period greater than 30 days, greater than 60 days, greater than 90 days, greater than 120 days, greater than 180 days, or greater than 1 year. In certain embodiments degradation of a material, structure, device, or device component is said to be complete when at least 80% by mass has degraded, when at least 85% by mass has degraded, when at least 90% by mass has degraded, when at least 95% by mass has degraded, or when at least 99% by mass has degraded. The biodegradation rate depends upon several factors, both environmental and material. Non-limiting examples of environmental factors influencing biodegradation rates include temperature, pH, oxygen concentrations, and microbial and enzymatic activities. Non-limiting examples of material properties influencing biodegradation rates include degree of branching of the polymer chains, the presence and amount of hydrophilic groups, stereochemistry, molecular weight, the degree of crystallinity, the crosslinking, surface roughness, and the surface to volume ratio.

The term "time-limited", as used herein, means that the material, structure, device, or device component degrades, breaks down, or loses some aspect of intended function over time. Like the biodegradable materials, structures, devices, or device components, the time-limited materials, structures, devices, or device components also may be referred to as being "transient". In some embodiments this can be via biodegradation. Time-limited can mean the degradation occurs by other intrinsic or exogenous means, such as specific changes in physiological conditions, pH, or temperature. In some cases time-limited materials do not begin to degrade or do not begin to significantly degrade until after a specific stimulus, i.e. an electrical, ultrasonic, or chemical signal may be employed to initiate degradation of one or more materials such that degradation can be initiated at a specific time that need not be predetermined. The degradation of time-limited materials can occur via hydrolysis, oxidation, reduction, enzymatic degradation, radicals, Norrish type I mechanisms, Norrish type II mechanisms, or by other mechanisms known in the art such as the biodegradation of polyethylene or paraffin as described in Albertsson et al. (1987), *Polymer Degradation and Stability*, 18:73-87.

The term "carbon nanomaterial", as used herein, refers to a class of structures comprising carbon atoms and having at least one dimension between one nanometer and one micron. In an embodiment, at least one dimension of the carbon nanomaterial is between 2 nm and 1000 nm Carbon nanomaterials include allotropes of carbon such as single walled nanotubes (SWNTs), multiwalled nanotubes (MWNTs), nanorods, single walled and/or multiwalled fullerenes, graphite, graphene, carbon fibers, carbon films, carbon whiskers, and diamond, and all derivatives thereof.

The term "coincident", as used herein, refers to the relative position of two or more objects, planes or surfaces, for example a surface that is positioned within or is adjacent to a layer, such as a functional layer, substrate layer, or other layer.

A "component", as used herein, broadly refers to a material or individual component used in a device. An "interconnect" is one example of a component and refers to an electrically conducting material capable of establishing an electrical connection with a component or between components. An interconnect may establish electrical contact between components that are separate and/or can move regarding each other. Depending on the desired device specifications, operation, and application, an interconnect is made from a suitable material. For applications where a high conductivity is required, typical interconnect metals may be used, including but not limited to copper, silver, gold, aluminum and the like, and alloys. Suitable conductive materials further include semiconductors, such as silicon and GaAs and other conducting materials such as indium tin oxide. In certain embodiments the interconnect is an organic semiconductor, preferably a polymeric organic semiconductor.

An interconnect that is "stretchable" or "flexible" is used herein to broadly refer to an interconnect capable of undergoing a variety of forces and strains such as stretching, bending and/or compression in one or more directions without adversely impacting electrical connection to, or electrical conduction from, a device component. A stretchable interconnect may be formed of a relatively brittle material, such as GaAs, yet remain capable of continued function even when exposed to a significant deformatory force (e.g., stretching, bending, compression) due to the interconnect's geometrical configuration. In an exemplary embodiment, a stretchable interconnect may undergo strain larger than 1%, optionally 10% or optionally 30% or optionally up to 100% without fracturing. In an example, the strain is generated by stretching an underlying elastomeric substrate to which at least a portion of the interconnect is bonded. For certain embodiments, flexible or stretchable interconnects include interconnects having wavy, meandering or serpentine shapes.

The term "compression", as used herein, is similar to the strain, but specifically refers to a force that acts to decrease a characteristic length, or a volume, of a substrate, such that $\Delta L < 0$.

The term "conformable", as used herein, refers to a device, material or substrate which has a bending stiffness sufficiently low to allow the device, material or substrate to adopt a desired contour profile, for example a contour profile allowing for conformal contact with a surface having a pattern of relief or recessed features. In certain embodiments, a desired contour profile is that of a tissue in a biological environment, for example heart tissue.

The term "conformal contact" refers to contact established between a device and a receiving surface, which may for example be a target tissue in a biological environment. In one aspect, conformal contact involves a macroscopic adaptation of one or more surfaces (e.g., contact surfaces) of an implantable device to the overall shape of a tissue surface. In another aspect, conformal contact involves a microscopic adaptation of one or more surfaces (e.g., contact surfaces) of an implantable device to a tissue surface resulting in an intimate contact substantially free of voids. In an embodiment, conformal contact involves adaptation of a contact surface(s) of the implantable device to a receiving surface(s) of a tissue such that intimate contact is achieved, for example, wherein less than 20% of the surface area of a contact surface of the implantable device does not physically contact the receiving surface, or optionally less than 10% of a contact surface of the implantable device does not physically contact the receiving surface, or optionally less than 5% of a contact surface of the implantable device does not physically contact the receiving surface. Conformal contact includes small areas, such as on the micron-scale (e.g. capillaries) and large area conformal contact, for example, such as in the peritoneal cavity, thoracic cavity or inside of a ventricle in the heart. For example, large areas with conformal contact between a tissue and device component can be over an area greater than or equal to 1000 mm$^2$, and optionally greater than or equal to 10,000 mm$^2$.

A "device component", as used herein, refers to an individual component within a device. Device components include, but are not limited to, a paving layer of the device or an electrical component of the device. Examples include, but are limited to, photodiode, LED, TFT, electrode, semiconductor, other light-collecting/detecting components, transistor, chemFET, mosFET, integrated circuit, storage and/or memory device, battery, piezoelectic system, power generation means, contact pad capable of receiving a device component, thin film devices, circuit elements, control elements, microprocessors, transducers and combinations thereof. A device component can be connected to one or more contact pads as known in the art, such as metal evaporation, wire bonding, application of solids or conductive pastes, for example.

"Electrical device" refers to a device incorporating a plurality of device components, and includes large area electronics, printed wire boards, integrated circuits, device components arrays, biological and/or chemical sensors, physical sensors (e.g., temperature, light, radiation, flow, shear, etc.), solar cell or photovoltaic arrays, display arrays, optical collectors, systems and displays.

The term "dielectric", as used herein, refers to a non-conducting or insulating material. In an embodiment, an inorganic dielectric can be a dielectric material substantially free of carbon. Specific examples of inorganic dielectric materials include, but are not limited to, silicon nitride and silicon dioxide.

The term "elastomer", as used herein, refers to a polymeric material which can be stretched or deformed and return to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers useful include, but are not limited to, thermoplastic elastomers, styrenic materials, olefenic materials, polyolefin, polyurethane thermoplastic elastomers, polyamides, natural rubbers, synthetic rubbers, PDMS, polybutadiene, polyisobutylene, poly(styrene-butadiene-styrene), vinyls and blends, polyurethanes, polychloroprene and silicones. In some embodiments, an elastomeric stamp can be an elastomer. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly (phenyl methyl siloxane), silicon modified elastomers, thermoplastic elastomers, styrenic materials, olefenic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a flexible polymer is a flexible elastomer.

The term "electrical contact", as used herein, refers to the ability of two or more materials and/or structures that can transfer charge between them, such as in transferring electrons or ions. Electrical communication refers to a configuration of two or more components such that an electronic signal or charge carrier can be directly or indirectly transferred from one component to another. As used herein, electrical communication includes one way and two way electrical communication. In some embodiments, components in electrical communication are in direct electrical communication wherein an electronic signal or charge carrier is directly transferred from one component to another. In some embodiments, components in electrical communication are in indirect electrical communication wherein an electronic signal or charge carrier is indirectly transferred from one component to another via one or more intermediate structures, such as circuit elements, separating the components.

The term "electronic device", as used herein, refers to devices such as integrated circuits, imagers or other opto-electronic devices. Electronic device may also refer to a component of an electronic device such as passive or active components such as a semiconductor, interconnect, contact pad, transistors, diodes, LEDs, circuits, etc. Devices disclosed herein may relate to the following fields: collecting optics, diffusing optics, displays, pick and place assembly, vertical cavity surface-emitting lasers (VCSELS) and arrays thereof, LEDs and arrays thereof, transparent electronics, photovoltaic arrays, solar cells and arrays thereof, flexible electronics, micromanipulation, plastic electronics, displays, pick and place assembly, transfer printing, LEDs, transparent electronics, stretchable electronics, and flexible electronics.

The term "encapsulate", as used herein, refers to the orientation of one structure such that it is at least partially, and sometimes completely, surrounded by one or more other structures. "Partially encapsulated" refers to the orientation of one structure such that it is partially surrounded by one or more other structures. "Completely encapsulated" refers to the orientation of one structure such that it is completely surrounded by one or more other structures. The invention includes implantable devices having partially or completely encapsulated electronic devices, device components and/or inorganic semiconductor components and/or electrodes.

The term "endoluminal", as used herein, refers to or describes objects that can be placed inside or moved through a lumen or a body passageway in a human or animal body. A lumen or a body passageway can be an existing lumen or a lumen created by surgical intervention, trauma or a disease process. As used in this specification, the terms "lumen" or "body passageway," and "vessel" should have a broad meaning and encompasses any duct (e.g., natural or iatrogenic) or cavity within the human body and can include a member selected from the group comprising: blood vessels, respiratory ducts, gastrointestinal ducts. The terms "endoluminal device" or "endoluminal biomedical implant" describe devices that can be placed inside or moved through any such lumen.

The term "fluid communication", as used herein, refers to the configuration of two or more components such that a fluid (e.g., a gas or a liquid) is capable of transport, flowing and/or diffusing from one component to another component. Elements may be in fluid communication via one or more additional elements such as tubes, containment structures, channels, valves, pumps or any combinations of these. In some embodiments, components in fluid communication are in direct fluid communication wherein fluid is capable of transport directly from one component to another. In some embodiments, components in fluid communication are in indirect fluid communication wherein fluid is capable of transport indirectly from one component to another via one or more intermediate structures separating the components.

The term "functional layer," as used herein, refers to a layer in a device or device component that imparts some functionality to the device or device component. The functional layer may be a thin film such as a semiconductor layer. Alternatively, the functional layer may have multiple layers, such as multiple semiconductor layers separated by support layers. The functional layer may have a plurality of patterned elements, such as interconnects running between device-receiving pads or islands. The functional layer may be heterogeneous or may have one or more properties that are inhomogeneous. "Inhomogeneous property" refers to a physical parameter that can spatially vary, effecting the position of the neutral mechanical surface (NMS) within the multilayer device The term "graft" or "graft material", as used herein, describes an object, device, or structure joined to or that can be joined to a body part to enhance, repair, or replace a portion or a function of that body part. A graft by itself or with additional elements, such as structural components, can be an endoluminal biomedical implant. The graft is a single material, a blend of materials, a weave, a laminate, or a composite of two or more materials. The graft can also be a polymer material that may be layered, sprayed, woven, or spun or otherwise applied onto a mandrel. Preferably, polymers, although added in layers onto the mandrel, after curing, result in one layer that encapsulates an endoluminal biomedical implant or woven graft. This also aids in decreasing the incidence of delamination of the resulting endovascular biomedical implant. The graft may be a cannular or tubular member, which acts substantially as an artificial vessel.

"Heterogeneous semiconductor elements" are multicomponent structures comprising a semiconductor in combination with one or more other materials or structures. Other materials and structures in this description may have elements, molecules and complexes, aggregates and particles thereof, that differ from the semiconductor in which they are combined, such as materials and/or structures having a different chemical compositions and/or physical states (e.g. crystalline, semicrystalline or amorphous states). Useful heterogeneous semiconductor elements include an inorganic semiconductor structure in combination with other semiconductor materials, including doped semiconductors (e.g., N-type and P-type dopants) and carbon nanomaterials or films thereof, dielectric materials and/or structures, and conducting materials and/or structures. Heterogeneous semiconductor elements of the present invention include structures having spatial homogeneous compositions, such as uniformly doped semiconductor structures, and include structures having spatial inhomogeneous compositions, such as semiconductor structures having dopants with concentrations that vary spatially in one, two or three dimensions (i.e. a spatially inhomogeneous dopant distribution in the semiconductor element).

The terms "island" and "device island", as used interchangeably herein, refer to a relatively rigid device element or component of an electronic device comprising multiple semiconductor elements or active semiconductor structures.

The terms "bridge" and "bridge structure", as used interchangeably herein, refer to stretchable or flexible structures interconnecting two or more device islands or one device island to another device component. Exemplary bridge structures include flexible semiconductor interconnects.

The terms "leakage current" or "leakage", as used interchangeably herein, refer to electric current that flows from an electronic device along an unintended path. Under certain conditions, leakage of sufficient current from an electronic device can damage the device and/or components thereof. In certain circumstances, leakage current can also or alternatively damage the "material into which it flows.

The term "optical communication" as used herein refers to a configuration of two or more devices or device components such that electromagnetic radiation can be directly or indirectly transferred from one component to another. As used herein, optical communication includes one-way and two-way optical communication. In some embodiments, components in optical communication are in direct optical communication wherein electromagnetic radiation is directly transferred from one component to another. In some embodiments, components in optical communication are in indirect optical communication wherein an electromagnetic radiation is indirectly transferred from one component to another via one or more intermediate structures, such as reflectors, lenses, or prisms, separating the components.

The term "biomedical implant", as used herein, refers to any replacement for a body part or for a function of that body part; or any device that monitors, enhances, or adds functionality to a tissue or physiological system.

The term "selectively permeable", as used herein, refers to a property of a material, such as a barrier layer in a device, to allow certain substances to pass through the material while preventing other substances from being passed through.

The terms "sensing element" and "sensor", as used interchangeably herein, refer to a device component useful as a sensor and/or useful for detecting the presence, absence, amount, magnitude, and/or intensity of a physical property, object, radiation, and/or chemical, biologic, or cellular element or component.

The term "spatially aligned", as used herein, refers to positions and/or orientations of two or more structures that are defined regarding each other. Spatially aligned structures may have positions and/or orientations that are preselected regarding each other, for example, preselected to within 1 micron, preferably for some applications to within 500 nanometers, and more preferably for some applications to within 50 nanometers.

The term "spatial variation", as used herein, refers to a parameter that has magnitude that varies over a surface, and is useful for providing two-dimensional control of component relief features, providing spatial control over the bendability of a device or device component.

The term "stretchable", as used herein, refers to the ability of a material, structure, device or device component to be strained without undergoing fracture. In some embodiments, a stretchable material, structure, device or device component may undergo strain larger than 0.5% without fracturing, for some applications strain larger than 1% without fracturing and for yet other applications strain larger than 3% without fracturing. A described herein, many stretchable structures are also flexible. Some stretchable structures (e.g., device components) are engineered to undergo compression, elongation and/or twisting to be able to deform without fracturing. Stretchable structures include thin film structures comprising stretchable materials, such as elastomers; bent structures capable of elongation, compression and/or twisting motion; and structures having an island-bridge geometry. Stretchable device components include structures having stretchable interconnects, such as stretchable electrical interconnects.

The term "substrate" refers to a material having a surface capable of supporting a structure, including an electronic device or electronic device component. A structure that is "bonded" to the substrate refers to a portion of the structure in physical contact with the substrate and unable to substantially move relative to the substrate surface to which it is bonded. Unbonded portions are capable of substantial movement relative to the substrate.

The term "thermal contact", as used herein, refers to the ability of two or more materials and/or structures that are capable of substantial heat transfer from the higher temperature material to the lower temperature material, such as by conduction. Thermal communication refers to a configuration of two or more components such that heat can be directly or indirectly transferred from one component to another. In some embodiments, components in thermal communication are in direct thermal communication wherein heat is directly transferred from one component to another. In some embodiments, components in thermal communication are in indirect thermal communication wherein heat is indirectly transferred from one component to another via one or more intermediate structures separating the components.

The term "thin layer," as used herein, refers to a material that at least partially covers an underlying substrate, wherein the thickness is less than or equal to 300 pm, less than or equal to 200 pm, or less than or equal to 50 pm. Alternatively, the layer is described in terms of a functional parameter, such as a thickness sufficient to isolate or substantially reduce the strain on the electronic device, and more particularly a functional layer in the electronic device sensitive to strain.

The term "tissue structure", as used herein, means any collection of cells and matrix, including but not limited to tendons, ligamentous attachment, intervertebral discs, post traumatic adhesions, or other stromal or parenchymal components.

The term "ultrathin," as used herein, refers to devices of thin geometries that exhibit extreme levels of bendability. In one embodiment, ultrathin refers to circuits having a thickness less than 1 pm, less than 600 nm or less than 500 nm. In an embodiment, a multilayer device that is ultrathin has a thickness less than 200 Mm, less than 50 pm, or less than 10 pm.

The terms "Young's modulus" and "modulus", as used interchangeably herein, refer to a mechanical property of a material, device or layer which refers to the ratio of stress to strain for a substance. Young's modulus may be provided by the expression;

$$E = \frac{\text{(stress)}}{\text{(strain)}} = \left(\frac{L_0}{\Delta L}\right)\left(\frac{F}{A}\right)$$

where E is Young's modulus, $L_0$ is the equilibrium length, $\Delta L$ is the length change under the applied stress, F is the force applied and A is the area over which the force is applied. Young's modulus may also be expressed from Lame constants via the equation:

$$E = \frac{\mu(3\lambda + 2\mu)}{\lambda + \mu}$$

where $\lambda$ and $\mu$ are Lame constants. High Young's modulus (or "high modulus") and low Young's modulus (or "low modulus") are relative descriptors of the magnitude of Young's modulus in a material, layer or device. In some embodiments, a high Young's modulus is larger than a low Young's modulus, preferably 10 times larger for some applications, more preferably 100 times larger for other applications and even more preferably 1000 times larger for yet other applications. "Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire layer of material. "Low modulus" refers to materials having a Young's modulus less than or equal to 10 MPa, less than or equal to 5 MPa, or optionally less than or equal to 1 MPa and optionally for some applications less than or equal to 0.1 MPa.

II. Electro-polymeric Endoluminal Paving and Sealing (ePEPS)

Methods for electropolymeric endoluminal paving and sealing (ePEPS) involve application of a polymeric material to the interior surface of a blood vessel, tissue lumen or other hollow space. The materials may also be applied to tissue contacting surfaces of implantable medical devices, preferably capable of monitoring performance of the implanted device, e.g. a ventricular assist device (VAD).

The polymeric material forms a polymeric scaffold, which can act as a support, barrier, diagnostic platform, or therapeutic release device or combination thereof. The polymeric scaffold can support, or function as, one or more integrated electronic devices that can locally monitor or alter fluid, tissue or organ function.

In general, electro-polymeric endoluminal paving and sealing (ePEPS) involves the introduction of a polymeric material onto a selected location on a tissue surface or a tissue-contacting surface of an implantable medical device. Typically, the polymeric material is in a fluent or sufficiently fluent state when introduced to the site. The fluent polymeric material may be molded to provide a coating having desired surface or shape characteristics. The polymer is biocompatible and in some cases biodegradable or bioerodible. The polymeric material contains one or more integrated electronic components or can function as an electronic device. The electronic components can be co-administered with the polymeric material or administered prior to or subsequent to the administration of the polymeric material. In some embodiments, the polymeric material and one or more electronic components are combined prior to administration to the site, such as in the form of a composite.

The tissue surface can be an internal or external surface, and can include the interior of a tissue lumen or hollow space whether naturally occurring or occurring as a result of surgery, percutaneous techniques, trauma or disease. The polymeric material is then reconfigured to form a coating or "paving" layer in intimate and conforming contact with the interior surface. The resulting paving layer optionally has a sealing function. As used herein, the term "sealing" or "seal" means a coating of sufficiently low porosity that the coating provides a barrier function. The term "paving" generally refers to coatings wherein the coatings are porous or perforated or are of a low porosity "sealing" variety.

The device includes a polymeric scaffold (e.g., the polymeric matrix in the non-fluent state) and one or more integrated electronic components or devices. The integrated electronic components are capable of locally monitoring, enhancing, attenuating, and/or impacting the function of an organ or organ component or are capable of storing, transmitting and/or receiving data. In some embodiments, the integrated electronic devices are biodegradable or bioerodible. In some embodiments, the polymeric scaffold serves as a controlled release matrix or contains a controlled release polymer matrix, capsule or reservoir means for delivery of one or more therapeutic or diagnostic agents. The polymeric matrix in the non-fluent state can exhibit a range of mechanical stiffness from very rigid to elastomeric depending upon the application.

A. The Polymeric Scaffold

In ePEPS, the polymeric material forms a polymeric scaffold for supporting one or more integrated electronic components or is composed of one or more integrated electronic components as part of the polymer layer.

The terms "polymeric scaffold", "paving layer" and "composite" are generally used interchangeably herein.

A polymeric scaffold is formed at the desired site. In one embodiment, the polymeric material is stimulated to render it sufficiently fluent to make conformal contact with the surface to be coated without damaging the integrated electronic component. The fluent polymeric material can be contacted with the surface to be paved, and the polymer is then allowed to return to its non-fluent state, thereby providing a polymeric scaffold for the integrated electronic component paved onto the surface. The coating preferably has a thickness on the tissue surface on the order of 0.001-1.0 mm; however, coatings having a thickness outside that range may be used as well.

The polymeric scaffold generally provides some useful function, such as providing local structural support, providing improved surface characteristics, providing improved flow, providing a selectively permeable or non-selective barrier, and/or sealing lesions. In other embodiments the polymeric scaffold is primarily used for supporting one or more components, including one or more integrated electronic components.

All or part of the polymeric scaffold forms a conformal contact with a tissue surface.

In some embodiments the polymeric scaffold imparts function to the smart biomedical implant. For instance, the polymeric scaffold may provide support for an organ or organ component or may serve as a seal or barrier. In yet other embodiments the polymeric scaffold may also serve as a drug, biologic or cell delivery matrix. A variety of materials can be used for the polymeric scaffold, depending on the purpose, i.e. structural, adhesive, barrier, cell, or drug delivery. For those applications where structure is required, a polymer is selected which has appropriate mechanical and physical properties.

It is preferred the polymer be biodegradable over a period of time. The desired time depends upon the application. This may be a few days, weeks, or months. An advantage of the polymeric materials is they can be tailored to shape the polymer into uneven surface interstices, while maintaining a smooth surface with good flow or other tissue compatibility characteristics.

Although described herein principally with reference to polymeric materials, it is to be understood that other materials may also be used to form the scaffold. Relatively low molecular weight organic compounds, such as common sugars (e.g. sucrose), cast from concentrated, warm aqueous solution to set up as monolithic solids in situ and erode with minimal swelling or fragmentation may be used in place of a polymeric material. Inorganic compounds formed by ion exchange, such as polysilicic acid salts, degradable bioceramics, bioglass, and "plasters" which degrade by surface erosion but which set in situ can also be used.

For those applications where the purpose does not require structural support properties, the polymeric scaffold may be formed of a material that is bioadhesive, or impermeable to molecules of specified molecular weights, or highly permeable, releasing incorporating drug over a desired period of time, and consisting of as little as a single layer of polymer. The paving material is preferably a homopolymer, or a binary or tertiary copolymer, however, copolymers having more than three constituents are intended to be included as well. The paving material may also be made of blends of these polymers.

The selection of the polymeric scaffold material is determined by whether it functions as a coating, bandage, adhesive, drug or cell delivery device, or mechanical support role. Further, the choice of polymer must appropriately balance the structural and geometric integrity needed against the appropriate rate of biodegradation or bioerosion over the time targeted to prevent an undesirable reaction. Sometimes, the material may be the same for different purposes where the ultimate in vivo geometry of the polymer dictates the final function of the polymeric scaffold.

Exemplary Configurations

Figure 1:
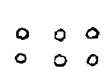
FIG. 1 is an illustration of an amorphous geometry of the ePEPS polymer coating before and after deployment.
Figure 1:
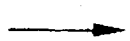
Figure 1:
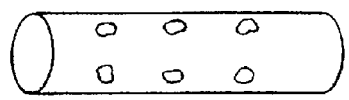
Figure 2:
FIG. 2 is an illustration of a stellate geometry of the ePEPS polymer coating before and after deployment.
Figure 2:
Figure 2:
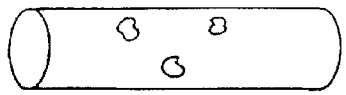
Figure 3:
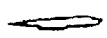
FIG. 3 is an illustration of a linear leathered polymer strip applied to "one" wall before and after deployment.
Figure 3:
Figure 3:
Figure 4:
FIG. 4 is an illustration of a large patch of sprayed on polymer material before and after deployment.
Figure 4:
Figure 4:
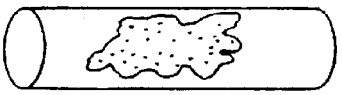
Figure 5:
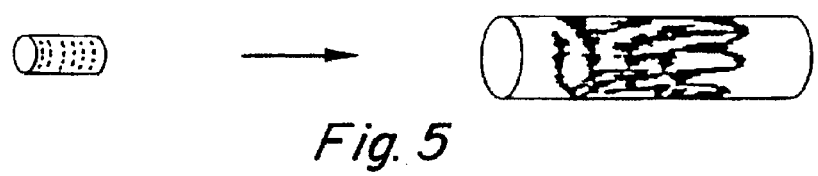
FIG. 5 is an illustration of a porous tubular form geometry before and after deployment.
Figure 6:
FIG. 6 is an illustration of a spot geometry of the ePEPS process before and after deployment.
Figure 7:
FIG. 7 is an illustration of a spiral form application of the ePEPS process before and after deployment.
Figure 8:
FIG. 8 is an illustration of an arcuate (radial, arc) patch geometry of the ePEPS polymer before and after deployment.
Figure 9A:
FIGS. 9A-G are cross-sectional images of paving layers or devices with admixed electronics showing the distribution of the electronics in the paving layers. The electronics in the devices depicted in FIG. 1-8 may have any of the configurations depicted in FIG. 9A-G.
Figure 9B:
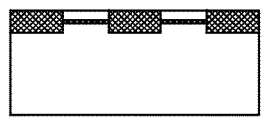
Figure 9C:
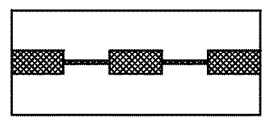
Figure 9D:
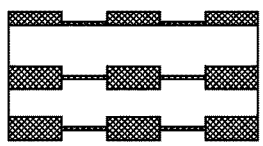
Figure 9E:
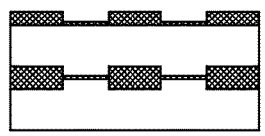
Figure 9F:
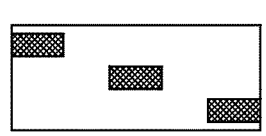
Figure 9G:
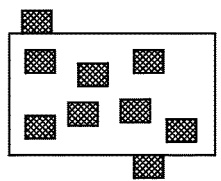

The polymeric materials forming the polymeric scaffold can be applied in custom designs, with varying thicknesses, lengths, and three-dimensional geometries (e.g. spot, stellate, linear, cylindrical, arcuate, spiral) to achieve varying finished geometries as depicted in FIGS. 1-8. For example, the paving material can be applied to the surface application of a vessel or organ and result in a device with an amorphous geometry (see, e.g. FIG. 1), stellate geometry (see e.g., FIG. 2), or spot geometry (see e.g., FIG. 6). Additional exemplary geometries for the resulting device include a linear feathered polymeric material strip applied to a particular area of the vessel wall as shown in FIG. 3. FIG. 4 shows a large patch of polymeric material which can be sprayed on using a variety of known techniques. Alternatively, such as when structural stability needs be imparted to the vessel, the resulting device may be in a porous tubular form, such as depicted in FIG. 5; a spiral form, such as illustrated in FIG. 7; or an arcuate (radial, arc) patch, such as shown in FIG. 8.

One or More Layers

The ePEPS can be applied as a single layer wherein all integrated electronics are contained within the paving material, or can be applied in multiple layer configurations wherein the integrated electronics are applied between polymer layers or are contained within some paving layers and not others.

The ePEPS can be used to completely occlude a tissue lumen. The thinner applications allow the polymeric scaffold to function as a coating, sealant and/or partitioning bather, bandage, and drug depot. Complex internal applications of thicker layers of polymer may provide increased structural support and, depending on the amount of polymer used in the layer, may serve in a mechanical role to maintain vessel or organ patency. Lesions of tissues that are mostly of fibromuscular components have a high degree of viscoelastic recoil. These lesions or tissues require using the process to apply an endomural coating of greater thickness or stiffness and extent to impart more structural stability resisting vessel radial compressive forces. This provides structural stability and applies generally for the maintenance of the intraluminal geometry of all tubular biological organs or substructure.

Materials

Broadly, the polymeric material can be a biocompatible polymeric material having a variable degree of fluency in response to a stimulus. Thus, the material can be such that it is substantially non-fluent in vivo. The material can be positioned adjacent to a tissue or non-tissue surface to be coated and then stimulated to render it fluent. The fluent polymeric material is contacted with the surface to be paved, and the polymer is then allowed to return to its non-fluent state, thereby providing a coating in the form of a biocompatible polymeric paving on the surface.

The basic requirements for the polymeric material are biocompatibility and the capacity to be applied in a solid or fluent state then chemically or physically reconfigured under conditions which can be achieved in vivo to yield a non-fluent polymeric material having defined characteristics for mechanical strength, permeability, adhesion, and/or release of incorporated materials.

The polymeric materials can be applied as polymers, monomers, macromers or combinations thereof, maintained as solutions, suspensions, or dispersions, referred to jointly as "solutions" unless otherwise stated. Polymeric materials can be thermosettable, thermoplastic, polymerizable in response to free radical or ion formation such as by photopolymerization, chemically or ionically crosslinkable (i.e., through agents such as glutaraldehyde or ions like calcium ions). Examples of means of solidifying or polymerizing the polymeric materials including application of exogenous means, application of light, ultrasound, radiation, or chelation, alone or in the presence of added catalyst, or by endogenous means, a change to physiological pH, diffusion of calcium ions (e.g., alginate) or borate ions (e.g., polyvinyl alcohol) into the polymeric material, or change in temperature to body temperature (37° C.). Polymeric materials may also be activatable by ultrasound or other exogenous energy means.

Although either non-biodegradable or biodegradable materials can be used, biodegradable materials are preferred. For application to tissues to prevent inflammation, enlargement and/or over-proliferation, it is preferred to use polymers degrading substantially within two months, six months, or twelve months after implantation. For prevention of adhesions or controlled release, the time over which degradation occurs should be correlated with the time required for healing, i.e., generally in excess of two weeks but less than six months.

Suitable materials are commercially available or readily synthesizable using methods known to those skilled in the art. These materials include: soluble and insoluble, biodegradable and non-biodegradable natural or synthetic polymers. These can be hydrogels or thermoplastics, homopolymers, copolymers or blends, natural or synthetic. As used herein, a hydrogel is defined as an aqueous phase with an interlaced polymeric component, preferably with 90% of its weight as water. The following definition is from the Dictionary of Chemical Terms, 4th Ed., McGraw Hill (1989): Hydrogel: a colloid in which the disperse phase (colloid) has combined with the continuous phase (water) to produce a viscous jellylike product, for example, coagulated silicic acid. An organogel is defined as an organic phase with an interlaced polymeric component, preferably with 90% of its weight as organic solvent. Preferred solvents include non-toxic organic solvents, such as dimethyl sulfoxide (DMSO), propylene glycol, polyethylene glycols, ethanol, N-methyl-2-pyrrolidone, glycofurol, Solketal™, glycerol formal, acetone, and tetrahydrofurfuryl alcohol, diglyme, dimethyl isosorbide, ethyl lactate, and mineral and vegetable oils. The preferred polymers are synthetic polymers, formable or synthesizable in situ, with controlled synthesis and degradation characteristics.

Natural Polymers

Representative natural polymers include proteins, such as zein, modified zein, casein, gelatin, gluten, serum albumin, elastin, fibronectin, fibrin, or collagen, and polysaccharides, such as cellulose, dextrans, hyaluronic acid, polymers of acrylic and methacrylic esters and alginic acid, and cellulosics. Natural gums may be utilized, such as Guar gum, carageenen, Okra gum, locust bean gum, honey locust gum, tara gum, sterculia foetida, khaya gum, and other natural gums, such as described in Avichat el al., "Recent Investigations of Plant Based Natural Gums, Mucilages and Resins in Novel Drug Delivery Systems, Ind. *J. Pharm. Edu. Res.,* 24(a):86-99 (2010). These may be utilized, although they are somewhat less desireable due to higher levels of variability in the characteristics of the final products, and in degradation following administration. Synthetically modified natural polymers include alkyl celluloses, hydroxyalkyl celluloses, cellulose ethers, cellulose esters, and nitrocelluloses, acrylic or methacrylic esters of above natural polymers to introduce unsaturation into the biopolymers.

Synthetic Polymers

Representative synthetic polymers are: poly(hydroxy acids) such as poly(lactic acid), poly(glycolic acid), and poly(lactic acid-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivatized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly (hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-coaprolactone), derivatives, copolymers and blends thereof. Synthetic polymers can include polyesters, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polysiloxanes, polyurethanes and copolymers thereof. Other polymers include celluloses such as methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, acrylates such as poly(methyl methacrylate), poly(ethyl methacrylate), poly(butyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(vinyl acetate), polyvinyl chloride, polystyrene, polyvinyl pyrrolidone, and polyvinylphenol. Representative bioerodible polymers include polylactides, polyglycolides and copolymers thereof, poly(hydroxy butyric acid), poly(hydroxyvaleric acid), poly(lactide-co-caprolactone), poly[lactide-co-glycolide], polyanhydrides, polyorthoesters, derivatives, blends and copolymers thereof. As used herein, "derivatives" include polymers having substitutions, additions of chemical groups, for example, alkyl, alkylene, hydroxylations, oxidations, and other modifications routinely made by those skilled in the art.

Examples of preferred biodegradable polymers include polymers of hydroxyacids such as lactic acid and glycolic acid, and copolymers with PEG, polyanhydrides, poly(ortho)esters, polyurethanes, poly(butyric acid), poly(valeric acid), poly(lactide-coaprolactone), blends and copolymers thereof. Examples of preferred non-biodegradable polymers include ethylene vinyl acetate, poly(meth)acrylic acid, polyamides, copolymers and mixtures thereof. The biodegradable materials degrade either by enzymatic hydrolysis or exposure to water in vivo, or by surface or bulk erosion.

These polymers can be obtained from sources such as Sigma Chemical Co., St. Louis, Mo., Polysciences, Warrenton, Pa., Aldrich, Milwaukee, Wis., Fluka, Ronkonkoma, N.Y., and BioRad, Richmond, Calif. or else synthesized from monomers obtained from these suppliers using standard techniques.

In some embodiments the materials forming the polymeric scaffold polymerize or alter viscosity as a function of temperature. Poly(oxyalkene) polymers and copolymers such as poly(ethylene oxide)-poly(propylene oxide) (PEO-PPO) copolymers, and copolymers and blends of these polymers with polymers such as poly(alpha-hydroxy acids), including, but not limited, to lactic, glycolic and hydroxybutyric acids, polycaprolactones, and polyvalerolactones, can be synthesized or commercially obtained. Polyoxyalkylene copolymers are described by U.S. Pat. Nos. 3,829,506; 3,535,307; 3,036,118; 2,979,578; 2,677,700; and 2,675,619, the teachings of which are incorporated herein. Polyoxyalkylene copolymers are sold by BASF and others under the tradename Pluronic™. Preferred materials include F-127, F-108, and for mixtures with other gel materials, F-67. These materials are applied as viscous solutions at room temperature or lower which solidify at the higher body temperature. Another example is a low $T_m$ and low $T_g$ grade of styrene-butadiene-styrene block copolymer from Polymer Concept Technologies, C-Flex™. Polymer solutions that are liquid at an elevated temperature but solid at body temperature can also be utilized. Thermosetting biodegradable polymers for in vivo use are described in U.S. Pat. No. 4,938,763 to Dunn, et al.

In some embodiments, the polymer forming the polymeric scaffold can be crosslinked by metal atoms. In some embodiments the metal atoms or ions are natural components of blood and body tissue. Several divalent ions including calcium, barium, magnesium, copper, and iron are normal constituents of the body tissues and blood. These ions can be used to ionically crosslink polymers such as the naturally occurring polymers collagen, fibrin, elastin, agarose, agar, polysaccharides such as hyaluronic acid, hyalobiuronic acid, heparin, cellulose, alginate, curdlan, chitin, and chitosan, and derivatives thereof cellulose acetate, carboxymethyl cellulose, hydroxymethyl cellulose, cellulose sulfate sodium salt, and ethylcellulose.

In some embodiments the polymeric scaffold is crosslinked by application of radiation. Materials that can be crosslinked using light, ultrasound or radiation are those materials which contain a double bond or triple bond, preferably with an electron withdrawing substituent attached to the double or triple bond. Examples of suitable materials include the monomers polymerized into poly(acrylic acids) (i.e., Carbopols™), poly(acrylates), Eudragits™ (a diverse range of polymethacrylate-based copolymers, which include anionic, cationic, and neutral copolymers based on methacrylic acid and methacrylic/acrylic esters or their derivatives), polyacrylamides, polyvinyl alcohols, acrylated polyethylene glycols, and ethylene vinyl acetates. Photopolymerization requires a photosensitizer, photoinitiator or both, any substance that either increases the rate of photoinitiated polymerization or shifts the wavelength at which polymerization occurs. The radiolysis of olefinic monomers results in the formation of cations, anions, and free radicals, all of which initiate chain polymerization, grafting and crosslinking and can polymerize the same monomers as with photopolymerization. Photopolymerization can also be triggered by applying appropriate wavelength to a cyclo-dimerizable systems such as Coumarin and Cinnamic acid derivatives. Alpha-hydroxy acids backbone can be activated to carbonium ion. COOH or $SO_3H$ functionality can be inserted that can be subsequently reacted to amine containing ligands Any amino containing polymer can be covalently crosslinked using a dialdehyde such as glutaraldehyde, or succindialdehyde. Examples of useful amino containing polymers include polypeptides and proteins such as albumin, and polyethyleneimine Peptides having specialized function, can also be covalently bound to these materials, for example, using crosslinking agents, during polymerization.

Polymers with free carboxylic acid or other anionic groups (e.g., sulfonic acid), such as the acrylic acid polymers noted above, can be used alone or added to other polymeric formulations to enhance tissue adhesiveness. Alternatively, materials that have tissue binding properties can be added to or bound to the polymeric material. Peptides with tissue adhesion properties are discussed below. Lectins that can be covalently attached to a polymeric material to render it target specific to the mucin and mucosal cell layer could be used. Useful lectin ligands include lectins isolated from: *Abrus precatroius, Agaricus bisporus, Anguilla anguilla, Arachis hypogaea, Pandeiraea simplicifolia, Bauhinia purpurea, Caragan arobrescens, Cicer arietinum, Codium fragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Limulus polyphemus, Lysopersicon esculentum, Maclura pomifera, Momordica charantia, Mycoplasma gallisepticum, Naja mocambique,* and the lectins Concanavalin A, Succinyl-Concanavalin A,

*Triticum vulgaris, Ulex europaeus* I, II and III, *Sambucus nigra, Maackia amurensis, Limax fluvus, Homarus americanus, Cancer antennarius*, and *Lotus tetragonolobus*.

The attachment of any positively charged ligand, such as polyethyleneimine, polylysine or chitosan to any polymeric chain may improve bioadhesion due to the electrostatic attraction of the cationic groups to the net negative charge of the mucus. A surfactant-like molecule bearing positive charge and a hydrophobic core would be compatible with the bilayer membrane. This molecule distributes its core and the positive charge to minimize energy of interaction and hence is more tissue adhesive. The mucopolysaccharides and mucoproteins of the mucin layer, especially the sialic acid residues, are responsible for the negatively charged surface layer. Any ligand with a high binding affinity for mucin could also be covalently linked to the polymeric material.

Polymeric materials can also be tissue adhesives. In one form, fibrin is used. This has the advantage it can be formed easily in situ using the patient's own fibrinogen, blood or serum, by addition of thrombin and calcium chloride. The materials described above can also be used. Other polymeric tissue adhesives commercially available include cyanoacrylate glues, GRF (Gelatin-resorcinol-formaldehyde) and polyethyleneglycol-poly(lactic acid and/or glycolic acid)-acrylates, both of which are applied as liquids and then photopolymerized.

Barrier Function

The polymeric material can be designed to achieve a controlled or selective permeability, i.e. as a barrier function, either for control of materials within the cavity or into the tissue or for release of incorporated materials. This may be a one-way barrier, a two-way barrier or dual function, as well. The barrier layer of a device may have spatially patterned permeable regions, impermeable regions or a combination of both permeable regions and impermeable regions. The bather layer may also prevent cellular, microorganisms or other biologics from passage through or migration into the barrier layer.

The polymeric material may be selectively permeable and allows one or more target chemicals, molecules and/or biomolecules to be passed through the material while preventing water, ionic solutions, bodily fluids, salts, proteins and other substances from being passed through the material.

There are three situations that the polymeric material is designed to achieve regarding materials present in the lumen: wherein there is essentially passage of only nutrients (small molecular weight compounds) and gases from the lumen through the polymeric material to the tissue lumen surface; wherein there is passage of nutrients, gases and macromolecules, including large proteins and most peptides; and wherein there is passage of nutrients, gases, macromolecules and cells. The molecular weight ranges of these materials are known and can be used to calculate the desired porosity. A macromolecule can be defined as having a molecular weight of greater than 1000 daltons; cells range from 600-700 nm to 10 microns, with aggregates of 30-40 microns in size.

For passage of cells, the material possesses or develops a macroporous structure. The polymeric scaffold can have a porosity from 1% to 80% or higher. The limitations on porosity are the degree of physical structural, i.e. material stability needed for a given use application versus the specifications needed for specific barrier exclusion functions for a given application. Similarly as relates to pore size, in some embodiments the polymeric scaffold can have an average pore size from 0.1-10 nm to allow fluid exchange and small molecule transport but exclude large molecules, multimeric proteins, macromolecular complexes, viral particles and the like. In other embodiments, pore size may range from 10 nm to 700 nm, i.e. to exclude cells but allow fluids, nutrients and molecular exchange. In further embodiments, pore size may range from 500 nm to 5 microns for fluid, molecular and other component exchange while excluding cells larger than 5 microns.

Decrease or Increase in Volume of the Electropaving Material

Under certain circumstances it may be useful to produce a polymer in situ which occupies a smaller volume than the solution from which it is applied, for example, as an adhesive for the cavity to hold the walls together. The polymerization can be accompanied by "syneresis" or expulsion of water from the polymer, during polymerization. Besides reducing mass of the product, this process may yield porous products that may be desirable for healing. Syneresis occurs when a polymerization reaction occurs with reaction of many fractional groups per unit volume (high crosslinking density or when dilute solutions of reactants are polymerized and the water in the formulation exceeds the intrinsic swelling capacity of the resulting polymer. The latter may occur, for example, when dilute solutions of PEG-diacrylate are polymerized (e.g., less than or equal to 5% macromer). The electro-paving materials described herein may decrease in volume passively or via electrical or other electrically actuatable cue.

Under certain circumstances it may be useful to produce a polymer in situ which occupies a larger volume than the solution from which it is applied, for example, as a volume expander or "tissue expander" to progressively create a new cavity to ease pressure or allow subsequent therapeutic application or natural ingress of fluid, gas or cells. Further swelling may act as a separator preventing contact of tissue surfaces that would otherwise be proximate. As such swellable materials may be delivered or polymerized in situ. Materials may be hygroscopic, dessicated, dehydrated or admixtures thereof. As for volume reduction above, conversely for volume expansion, the electro-paving materials described herein may expand passively or via electrical or other electrically actuatable cue.

Additives in the Electropaving Material

The polymers and copolymers may sometimes contain additives such as plasticizers (e.g., citrate esters), to improve their function, such as to reduce the temperature at which sufficient fluency is obtained. In addition, physical blends of polymers including the combinations of several different biostable and/or biodegradable polymers could be utilized in this process. Likewise the process allows polymeric composites or blends of the polymers described above incorporating separate polymeric, metallic, or other material domains to be introduced onto tissue or tissue contacting surfaces. Such domains may be present as randomly or uniformly distributed microparticles, microcapsules, nanoparticles, nanocapsules, or liposomes of uniform or random size shape or compositions.

B. Integrated Electronic Components or Devices

The integrated electronic components or devices can be positioned in the polymeric scaffold either homogenously or heterogeneously, and can be positioned at the top, bottom, or intermediate layers of the polymeric scaffold or as a mixture thereof. For example, FIGS. 9A-G illustrate a variety of suitable configurations of the electronic components in, on, under, etc the polymeric scaffold.

The integrated electronic devices and components can in some embodiments be repositioned or have the relative position within the polymeric scaffold adjusted after placement, i.e. while the polymeric scaffold is still in the fluid state the device or component can be moved or adjusted as needed to obtain desired positioning of the device or component.

The integrated electronic components may be incorporated in the paving article either continuously or discontinuously. The electronic elements may be repetitive, i.e. duplicative or multiple different types, that are mixed and laced at defined spacing based upon use.

The electronic components can be single, grouped or an integrated circuit; or a collection of integrated circuits, essentially forming a micro motherboard. An exemplary micro motherboard is depicted in FIG. 10C.

The electronic components can be stretchable structures, and/or include stretchable interconnects, such as stretchable electrical interconnects. One or more of the electronic components may be capable of elongation, compression and/or twisting motion. The electronic components may be configured having an island-bridge geometry.

The electronic components or devices may be resident or dispersed on, in, within, or a combination thereof, the polymeric scaffold, creating electronic elements varying depths or configuration within the paving device or layer. Such arrangements may be designed for structure or function significance or a combination thereof. In some embodiments the integrated electronic component is placed on the polymeric scaffold material in such a position and orientation to maintain intimate and conformal contact with the tissue surface after paving. Alternatively, the electronic component may be embedded within the interior of the polymeric scaffold, or may be positioned to contact the interior cavity of the hollow or tubular organ upon paving, i.e. the integrated electronic component may be an oxygen sensor or pressure sensor placed to sufficiently contact blood being pumped through the artery.

In some embodiments the integrated electronic component is supported on a polymeric scaffold positioned adjacent to a tissue or non-tissue surface to be coated.

Integrated electronic components are capable of providing a number of useful functions. In certain embodiments the integrated electronic component is capable of locally monitoring the function of the organ or organ component, i.e. is capable of monitoring pressure, temperature, acceleration, or flow rate. In some embodiments an integrated electronic component that locally monitors the organ or organ component is in conformal contact or sufficiently conformal contact with the tissue surface. In some embodiments the integrated electronic component is maintained in conformal contact with the tissue surface at least in part by the polymeric scaffold.

In some embodiments, an integrated electronic component is capable of providing a local stimulus to the tissue, i.e. is capable of delivering locally an electrical signal. For example, the integrated electronic components can be used to induce galvanotaxis or enhance or reduce local function. As shown in FIG. 11, the electronic components can produce an electric field (EF) which can either inhibit (restenosis) or enhance (stimulate) (wound healing) cell growth. Similarly the electric field can attract or inhibit the growth of bacteria (e.g. sterilize). In some embodiments an integrated electronic component is capable of locally sensing or detecting the presence of one or more chemical or biological agents.

Further, the integrated electronic components may be utilized for local heating, to alter the configuration of the polymer paving material, such as its configuration, nature or composition. The integrated electronic components may be utilized to actuate the polymeric material, or admix material within the one or more layers polymeric material. An example is the actuation of a material via contained electronics to locally release a drug, particle, imaging agent, or cell. Electronic components may also be utilized to locally create an antimicrobial or anti-infective environment by virtue of local heating and/or sterilization.

In some situations it is useful to store, receive, and/or transmit data via an integrated electronic component, i.e. an integrated electronic component may store data from a variety of sensors monitoring organ function and may at some later time wirelessly transmit stored data to a receiving device external to the patient. The components integrated into the polymeric scaffold may require a source of electrical power. In some embodiments an integrated electronic device includes a battery capable of providing sufficient power over the useful life of the implant. In some embodiments an integrated electronic component includes a means of receiving power wirelessly from an external source. In other embodiments the integrated electronic component is capable of generating electrical power using energy provided locally by the organ or organ component.

Examples of integrated electronic components include, but are not limited to, pizoelectic materials, converting mechanical energy to electrical energy or redox materials creating electrical voltage by virtue of chemical means, like a fuel cell.

The choice of specific electronic devices depends upon the application and the examples provided herein are not to be construed as limiting. In theory, any biocompatible integrated electronic device with sufficient mechanical stability and dimension can be employed. Further electronic components or devices even with limited or no biocompatibility may be employed as long as they are encapsulated within the polymeric material/scaffold so that the external elements of the polymeric material/scaffold are of sufficient biocompatibility for the given application.

The requirements for size, modulus, etc. depend upon the specific application. In some embodiments an integrated electronic component or device has a greatest dimension of less than 1,000 microns, less than 500 microns, less than 200 microns, less than 50 microns, less than 10 microns, or less than 1 micron.

Smart biomedical implants typically contain one or more biologically compatible integrated electronic devices that provide for monitoring, sensing, attenuation, communication, or power. Integrated electronic devices are preferably flexible, stretchable, or a combination of flexible and stretchable depending upon the demands of the application. Integrated electronic devices may maintain intimate conformal contact locally with the tissue of the organ or organ component. Foreign substances in the body may trigger an inflammatory response that can result in encapsulation of the implant with fibrous connective tissue increasing resistance at the interface between the tissue and the device or device component. In some embodiments, the integrated electronic device is formed of a material that does not trigger an inflammatory response or that triggers a minimal inflammatory response. In some embodiments all or part of the integrated electronic device is encapsulated in a barrier material that does not trigger an inflammatory response or that triggers a minimal inflammatory response. Many biologically compatible coating or barrier materials are known, such as gold, platinum, SU-8, Teflon, polyglycerols, or hydrophilic polymers such as polyethylene glycol (PEG) or phosphorycholine, cell membranes or cell membrane-like material, aluminum oxide ($Al_2O_3$), hydroxyapatite (HA), silicon dioxide (SiO$_2$), titanium carbide (TiC), titanium nitride (TiN), titanium dioxide (TiO$_2$), zirconium dioxide (ZrO$_2$).

Flexible Electronic Devices of Components

Flexible electronic devices or components of flexible electronic devices are in some embodiments formed of a material that is inherently flexible, i.e. a flexible organic polymer. Exemplary polymers include polyanilines, polycaprolactones, polylactic acids, copolymers and block-copolymers thereof. The polymers can be biocompatible or can be encapsulated with a biocompatible material as described above. In some embodiments the flexible electronic devices or components of a flexible electronic device are fabricated from materials that are not inherently flexible but are fabricated sufficiently thin to provide the desired level of flexibility. The components of the flexible electronic devices may be fabricated for instance out of thin layers of crystalline silicon. The silicon layer may have a thickness less than or equal to 100 microns, optionally less than or equal to 10 microns, optionally less than or equal to 1 micron, optionally less than or equal to 500 nm Flexible electronic devices may have a net bending stiffness less than or equal to $10^8$ GPa μm$^4$, optionally less than $10^7$ GPa μm$^4$, or optionally less than or equal to $10^6$ GPa μm$^4$. The integrated electronic devices and components can be fashioned from conducting or semiconducting materials that are degradable, corrodible, or otherwise time-limited. Integrated electronic devices and components can be made from magnesium, iron, silver, copper, tin, lead, actinide metals, lanthanide metals, alkali metals, alkaline-earth metals, noble metals, rare metals, rare-earth metals, or transition metals or alloys thereof. Integrated electronic devices and components can be made from a variety of materials and alloys such as those described in Ricker et al. (1994), "Corrosion of Metals" pgs. 669-728 in "Evaluation of Alternative In-Flight Fire Suppressants for Full-Scale Testing in Simulated Aircraft Engine Nacelles and Dry Bays. Section" edited by Grosshandler et al. NIST, 1994. The materials forming the integrated electronic device or component can be chosen based upon available rates of degradation or corrosion to choose the desired rate of degradation of the electronic device or component.

In some embodiments, electronic devices or components thereof are made flexible and/or stretchable by inclusion of a neutral mechanical surface to correspond to strain-sensitive layers or by selective use of strain isolation layers to isolate strain-sensitive layers from applied stresses and strains. In an example the electronic components or devices may reside in a neutral mechanical plane in a polymeric material or scaffold, where the surrounding material and/or layer contains a stretchable elastomer, such as for example anatural rubber, silicone rubber or polyurethane.

The devices can combine high quality electronic materials, such as aligned arrays of silicon nanoribbons and other inorganic nanomaterials; flexible and/or biodegradable electronic materials such as melanin; and ultrathin and elastomeric substrates, in multilayer neutral mechanical plane designs and with an optionally 'wavy' structural layout. The electronic devices may contain strain isolation layers that minimize or eliminate the influence of mechanical strain on device performance, thereby facilitating the use of such devices in a wide range of applications and of any arbitrary geometry. The integrated electronic devices may therefore be incorporated in shape-conforming biomedical implants without demonstrating strain-induced mechanical failures.

Biodegradable Electronic Devices or Components

In some embodiments all or part of the components of the integrated electronic device are biodegradable. In some embodiments the rate of degradation of all or some of the components is adjusted to coincide with the useful life of the device. A wide range of biodegradable materials may be used in the integrated electronic device (e.g., distinct biodegradable materials may be used for each component), and the physical properties of the biodegradable materials may mirror those of materials that have been used in traditional organic thin-film microelectronic applications. However, unlike traditional organic thin-film microelectronic applications, in some embodiments, the active layer of the integrated electronic device contains a semiconducting material that is biodegradable, such as thin or ultra-thin silicon, a polymer, a protein, and/or a pigment (e.g., melanin). More specifically, in certain embodiments, the active layer of the biodegradable electronic device contains a biodegradable, erodible or soluable semiconducting material, such as silicon, graphene, a polymer, a protein, carbon nanotubes, DNA, and/or an organic pigment. For example, the biodegradable semiconducting material of the active layer may be silicon, graphene, carbon nanotubes, DNA or melanin. The biodegradable semiconducting material of the active layer also may have aromatic amino acids and their oligomers/polymers, porphyrin based proteins, block copolymers of synthetic conducting polymers if biodegradable blocks are sufficiently frequent to generate low molecular weight fragments, and metallized biopolymers.

The integrated electronic device may in some embodiments contain a biodegradable dielectric layer. The biodegradable dielectric lay may be silk, or poly(glycerol-sebacate) ("PGS"), which is a synthetic flexible biodegradable elastomer; polydioxanone; and/or poly(lactic-co-glycolic acid) ("PLGA"). Each of these materials has desirable mechanical properties and is biodegradable.

Semiconductors

Use of the term "semiconductor" is consistent with this term in the art of microelectronics and electronic devices.

The polymeric material may include a semiconducting material, either as a formed electronic component or device, or as a constituent of a material forming an electronic component or device. Semiconducting materials include the range of elements and salts and/or oxides of these elements that may function as semiconductors including, but not limited to, silicon, germanium, gallium, boron, tin, lead, uranium, bismuth, barium, strontium, lithium, aluminum, indium, lanthanum, cadmium, copper, europium, platinum, nickel, mercury, silver, thallium, zinc. These materials may also be used singly or multiply as dopants. An example of doping includes DNA with admixed carbon, grapheme, or any of the listed semiconductor elements, their oxides or salts.

In some embodiments the semiconductor is an inorganic semiconductor. In some embodiments the semiconductor is an organic semiconductor. In some embodiments the semiconductor is a polymeric organic semiconductor. Useful inorganic semiconductors include those comprising element semiconductors, such as silicon, germanium and diamond, and compound semiconductors, such as group IV compound semiconductors such as SiC and SiGe, group III-V semiconductors such as AlSb, AlAs, Aln, AlP, BN, GaSb, GaAs, GaN, GaP, InSb, InAs, InN, and InP, group III-V ternary semiconductors alloys such as Al$_x$Ga$_{l-x}$As, group II-VI semiconductors such as CsSe, CdS, CdTe, ZnO, ZnSe, ZnS, and ZnTe, group I-VII semiconductors CuCl, group IV-VI semiconductors such as PbS, PbTe and SnS, layer semiconductors such as $PbI_2$, $MoS_2$ and GaSe, oxide semiconductors such as CuO and $Cu_2O$. The term semiconductor includes intrinsic semiconductors and extrinsic semiconductors doped with one or more selected materials, including semiconductor having p-type doping materials and n-type doping materials, to provide beneficial electronic properties useful for a given application or device. The term semiconductor includes composite materials comprising a mixture of semiconductors and/or dopants. Specific semiconductor materials useful for in some embodiments include, but are not limited to, Si, Ge, SiC, AlP, AlAs, AlSb, GaN, GaP, GaAs, GaSb, InP, InAs, GaSb, InP, InAs, InSb, ZnO, ZnSe, ZnTe, CdS, CdSe, ZnSe, ZnTe, CdS, CdSe, CdTe, HgS, PbS, PbSe, PbTe, AlGaAs, AlInAs, AlInP, GaAsP, GaInAs, GaInP, AlGaAsSb, AlGaInP, and GaInAsP. Porous silicon semiconductor materials are useful for applications of aspects described herein in the field of sensors and light emitting materials, such as light emitting diodes (LEDs) and solid state lasers. Useful organic semiconductors include acenes, perylenes, fullerenes, phthalocyanines, oligothiophenes, and substituted derivatives thereof. Particular organic semiconductor compounds include sexithiophene, α,ω-dihexylsexithiophene, quinquethiophene, quaterthiophene, α,ω-dihexylquaterthiophene, α,ω-dihexylquinquethiophene, bis (dithienothiophene), anthradithiophene, dihexylanthradithiophene, polyacetylene, polythienylenevinylene, $C_{60}$, [6,6]-phenyl-$C_{61}$-butyric acid methyl ester, copper(II) hexadecafluorophthalocyanine, and N,N'-bis (pentadecafluoroheptylmethyl)naphthalene-1,4,5,8-tetracarboxylic diimide Useful polymeric organic semiconductors include polyacetylenes, polydiacetylenes, polypyroles, polythiophenes, polyphenylenes, poly(arylene vinylenes), polyanilies, and copolymer and derivatives thereof. Particular polymeric organic semiconductors include poly(3-hexylthiophene), poly(phenylene vinylene), and poly(pyrrole). Organic semiconductors offer several advantages including inexpensive, easy shaping and manufacturing, a wide range of tunable properties via synthetic modifications, high degree of flexibility (especially in thin film devices), and their compatibility with a wide variety of substrates.

a. Sensors

In some embodiments the integrated electronic device can be a sensor. These can measure temperature, mechanical forces such as stress and strain, pressure; fluid flow properties such as flow rate and shear, electromagnetic fields, and chemical factors or variables, including pH, ion concentration, enzymes (presence of, activity of, or use of to measure other elements), and analyte concentrations. Sensors can be on the surface, inside a hollow or porous wall of the implant, or inside a device in communication with the body tissue via a conduit to the implant (solid, hollow, or porous). These sensors include, but are not limited to, four classes of principal transducers: potentiometric, amperometric, optical, and physiochemical. An amperometric sensor monitors currents generated when electrons are exchanged between a biological system and an electrode. Blood glucose sensors frequently are of this type.

Sensors in some embodiments function to transduce a biological signal into an electrical signal, optical signal, wireless signal, acoustic signal, etc. Useful sensing elements include, but are not limited to electrode elements, chemical or biological sensor elements, pH sensors, optical sensors, photodiodes, temperature sensors, capacitive sensors, strain sensors, acceleration sensors, movement sensors, displacement sensors, pressure sensors, acoustic sensors or combinations of these.

The sensor can be a biosensor specific for detecting the presence of one or more molecules. A biosensor includes at least a biological element for recognizing one or more biomolecules and a transducer for converting the biological signal into the desired output signal. For example, the biological element can include a cell receptor, a nucleic acid or aptamer, or an antibody or other element with analyte detection means and/or sensitivity. The transducer can include an electrode that receives an electrical signal directly from the biomolecule or a piezoelectric material that generates an electrical signal in response to the biomolecule. An exemplary biosensor is a blood glucose sensor consisting of an electrode material coated with the enzyme glucose oxidase. The enzyme breaks down blood glucose and the corresponding oxidation/reduction reaction generated a current in the electrode proportional to the amount of glucose in the blood.

The sensor can be a pressure sensor, such as the microscale pressure sensors described in U.S. Pat. No. 6,890,300 to Lloyed, et al., and U.S. Pat. No. 8,336,387 to Tai, et al., which can be made from flexible and/or stretchable materials.

The transducer converts the signal into a usable output. Exemplary transducers include, but are not limited to, electrochemical transducers (including potentiometric, amperometric, and conductimetric transducers), optical transducers (including flourescence, bioluminesencer), thermal transducers, and acoustic transducers, as known in the art. The transducer can include an electromagnetic actuator capable of generating an electric field, such as those described in U.S. Pat. No. 5,863,024 to Blind, et al.

A power source, such as a printed thin film lithium battery, a bioelectric battery or the piezoelectric power source described below, may be connected with the sensor to provide any required power.

The sensors may include means for transmitting a signal to monitoring means or directly to actuating means. The means for transmitting a signal may be hard wired or transmitted via radio waves or magnetic or mechanical means.

b. Data Storage and Signaling Means

Several devices, both external and internal, can receive and transmit signals from the sensors to the actuators. These may be radio transponders, light, or sound wave receivers and transmitters, or hard wired into the devices. Data storage may be incorporated in the polymeric scaffold, adjacent to the polymeric scaffold, or may be separate from the device, such as in a different location in the body or on the body. A strategy of nested loops may be utilized to store and/or interrogate or telemeter data.

The ultrasonic sensor described in U.S. Pat. No. 5,807,258 to Cimochowski, et al., can monitor the condition of a vascular graft. One or more transducers are provided either in a wall of the implant or adjacent to the implant to monitor the parameter. A conformal array transducer or a tilted element is used to monitor fluid flow or velocity through the implant based on the effect of the fluid on ultrasonic waves produced by the transducers. The conformal array transducer has a plurality of elements that curve around the implant and are excited with an input signal provided by an implantable electronics circuit, producing ultrasonic waves that propagate into the fluid flowing within the graft or vessel. Transit time or Doppler measurements are made using an appropriate number of these transducer to determine either fluid flow or velocity. Various implantable electronic circuits are provided that enable a selected transducer to be driven and to receive an ultrasonic signal or a pressure signal indicative of the status of fluid flow monitored by the transducer. The implanted electronic circuit is connected to an implanted radio frequency (RF) coil. An external coil connected to a power supply and monitoring console is coupled to the implanted RF coil to convey power and receive data signals from the transducer indicative of the parameter being monitored. Activatable means may be incorporated in the polymeric scaffold or device.

c. Power Sources and Power Storage

Soft batteries, such as printed batteries are manufactured using methods to create them disposable. These batteries contain no environmentally hazardous materials and can be disposed with the sensors with no special handling, such as circulation of batteries. This creates limitations on the material selections. Materials of the printed batteries cannot be changed to stand the high humidity and corroding atmosphere. A typical packaging solution for the soft batteries uses plastic or paper based electrically non-conductive material in making the package. Using of paper based package is not an option in the high humidity environment because the humidity and the salt would then absorb to the paper and short circuit the battery terminals. Some types of printed batteries may include wet electrolytes and they may be sealed within a plastic sheathing film to prevent liquid evaporation, and are therefore closed electrochemical cells. Being closed cells, these batteries may swell upon storage due to undesirable gas formed within the battery.

In some embodiments an integrated electronic component includes one or more power generation means capable of generating sufficient electrical energy to power the one or more integrated electronic components. The piezoelectric materials can convert the motion of the organ or organ component into an electrical current. Piezoelectric materials can include piezoelectric crystals such as gallium phosphate, quartz, and tourmaline, or thin films or nanoparticles made from piezoelectric ceramics such as barium titanate, lead zirconate, lead titanate, and/or lead zirconate titanate or organic piezoelectric materials such as polyvinylidene fluoride.

The piezoelectric material can be positioned within the polymeric scaffold such that the motion of the organ or organ component to which it adheres, i.e. the contraction of the muscular tissue causing a vibration or a bending of the piezoelectric, results in the generation of an electric current, such as described in Dagdeviren, et al., "Conformal piezoelectric energy harvesting and storage from motions of the heart, lung, and diaphragm," *PNAS*, 111(5): 1927-1932 (2014). In some embodiments, the electric current is provided directly to one or more integrated electronic components or optionally is used to charge a battery or a capacitor.

The power source can be an induction coil capable of being tuned to a preselected frequency. The induction coil can be in communication with a remote generator that is able to generate an oscillating magnetic field at the preselected frequency. The oscillating magnetic field is able to create a voltage across the induction coil to provide a source of power.

Integrated electronic devices and device components can be powered by one or more batteries, by transmitted power such as radiofrequency or magnetic, by integrated power generation means such as the piezoelectric power generators described, or by any combination thereof.

Methods of Making the Electronic Devices or Components

The integrated electronic devices can be made by any method suitable for microfabrication. One skilled in the art will recognize that the exact nature of the fabrication depends upon the flexible, stretchable, and or biodegradable electronic materials employed. In a preferred embodiment the integrated electronic devices are fabricated by transfer printing one or more of the device components onto a flexible substrate material.

C. Additional Components

Optional additions to the polymeric material such as barium, iodine or tantalum salts for X-ray radio-opacity allow visualization and monitoring of the coating.

The polymeric scaffold may support one or more controlled release devices for delivering one or more therapeutic, prophylactic, or diagnostic agents. Controlled release polymer systems are known in the art. In some embodiments the polymeric scaffold contains one or more of these controlled release polymer systems for delivering a therapeutic, prophylactic, or diagnostic agent. In some embodiments the controlled release system is capable of release of a therapeutic, diagnostic, or prophylactic agent in response to a particular stimulus, i.e. in response to the presence of a particular biomolecule, change in temperature, or change in pH. The controlled release system can be, for example, a liquid crystalline material such as those described in Herman et al., *Chemistry*, 15:117-124 (2009). Coupled to a biosensor having a transducer capable of producing an electric field, such a controlled release system is capable of delivering a therapeutic, prophylactic, or diagnostic agent in response to a specific molecule detected by the biosensor.

In the simplest of the embodiments described herein, the polymeric scaffold is formed of a material which is itself responsive to the environment, for example, to temperature or pH, which causes a change in the material, for example, an increase in pore size, effecting release of the therapeutic, prophylactic or diagnostic agent as needed. An example of such a situation is when the tissue around the implant becomes infected, changing both the temperature and the pH. Use of a temperature responsive material that increases porosity as the temperature increases can deliver antibiotic (or another drug) only when, or in an increased amount when, infection is present.

Any natural or synthetic, organic or inorganic molecule or mixture thereof can be delivered. Optionally, the device delivers drugs systemically to a patient in need thereof. In another embodiment, the construction and placement of the implant in a patient enables the localized release of drugs that may be too potent for systemic delivery. As used herein, drugs are organic or inorganic molecules, including proteins, nucleic acids, polysaccharides and synthetic organic molecules, having a bioactive effect, for example, anaesthetics, vaccines, chemotherapeutic agents, hormones, metabolites, sugars, immunomodulators, antioxidants, ion channel regulators, and antibiotics. The drugs can be in a single drug or drug mixtures and can include pharmaceutically acceptable carriers. In another embodiment, molecules are released in vitro in any system where the controlled release of a small (milligram to nanogram) amount of one or more molecules is required, for example, in the fields of analytic chemistry or medical diagnostics. Molecules can be effective as pH buffering agents, diagnostic agents, and reagents.

U.S. Pat. No. 5,797,898 to Santini, et al., describes implants for delivery of a wide variety of molecules Implants are miniaturized devices constructed using methods commonly applied to manufacturing integrated circuits such as ultraviolet (UV) photolithography, reactive ion etching, and electron beam evaporation. The implants provide control over the rate the molecules are released and the time at which release begins. The time of release can be controlled passively or actively.

III. Methods of Making and Using a. Application of Polymeric Materials

Generally, the polymeric material forming the polymeric scaffold is a biocompatible polymeric material having a variable degree of fluency in response to a stimulus or mechanical pressure, as described above. The material is substantially non-fluent in vivo upon completion of the coating process.

The material may be brought into the in vivo domain, i.e. animal or man or other living organism, in a non-fluent state. In this state it may either be continuous or discontinuous. Upon delivery and placement of the material to form paving article, the material may be actuated to reconfigure itself to form an adherent, intimately, conformal paving layer or article. As such, the material, in its fluent form or a conformable form, is positioned in contact with a tissue or device surface to be coated and then stimulated to render it non-fluent or conformed, as described herein.

The coating typically is applied to an endoluminal tissue surface such as the intima or media of an artery, the urethra, brain or the endocardium/myocardium using some type of catheter, trocar or scope. The coating material is preferably applied using a single catheter or similar device with single or multiple lumens. The catheter should be of relatively low cross-sectional area. A long thin tubular catheter manipulated using endoscopic guidance is preferred for providing access to the interior of organ areas. Alternatively the device may have direct vision capabilities via contained fiberoptics or actual tip cameras (CCD, C-MOS, etc) or via echo sensing, US or OCT sensing or imaging or GPS positioning systems.

During the step of positioning the paving material at the desired location, the location may be accessed by either invasive surgical techniques or by relatively non-invasive techniques such as laparoscopic procedures or percutaneous transluminal procedures. In one embodiment, the step in which the paving material is contacted with the tissue surface may be considered as a "molding" procedure in which the paving material is molded into substantially conforming contact with the body tissue before transitioning into a non-fluent coating on the surface.

Transfer from Non-Fluent to Fluent State or Vice-Versa

In some embodiments the polymeric material is non-fluent at body temperature but can be rendered fluent or sufficiently fluent by heating. For example, the viscosity in the fluent state may range from 1 cP up to $10^6$ cP. The material can be heated to render fluent, contacted with a tissue surface to be coated, and allowed to cool, thereby providing a non-fluent biocompatible polymeric coating on the tissue surface.

In some embodiments, the transition from a fluent state to a non-fluent state can be the result of a phase change in which the polymeric material goes from a solid to a liquid state, or in the alternative; or it may be the result of a viscosity change with the polymeric material remaining in a single phase throughout. In some embodiments, the polymer is applied in a fluent or sufficiently fluent state and is rendered non-fluent by crosslinking. In some embodiments the polymer is crosslinked by the application of heat, light, and/or chemical crosslinking agents. In some embodiments a fluent solution of monomers or prepolymers is reacted to form the polymer in situ. The polymerization reaction can be initiated by heat, light, and/or chemical catalyst. Other means may be utilized to create a fluent state (or non-fluent state), including but not limited to cooling, ultrasound, radiation, or application of electrical charge or magnetic fields.

The transition of the paving material from a non-fluent to a fluent state, and vice-versa, may involve a phase change in the material, however, such a phase change is not necessary. For example, in certain embodiments, the terms "non-fluent" and "fluent" are primarily relative descriptions of a material which undergoes a significant change in viscosity and flowability without undergoing an actual phase change. Alternatively, the transition of the material between its fluent and non-fluent states may be the result of an actual phase change in the material resulting either from the addition or removal of energy from the material.

Devices of Application of Paving Material

The paving material is applied to the tissue or device surface using any suitable device, such as catheters, trochars, tubular devices, syringes, and/or sprays, depending on the tissue surface or device to which it is applied. Suitable devices are known to those skilled in the art.

Application of the paving material may be accomplished by extruding a solution, dispersion, or suspension of monomers, polymers, macromers, or combinations thereof through a catheter to coat or fill a tissue surface or cavity, then controlling formation of the coating by introducing crosslinking agents, gelling agents or crosslinking catalysts together with the fluent material and altering the conditions such that crosslinking and/or gelling occurs.

When a balloon catheter is used, a flow of heated or chilled fluid into the balloon can alter the local temperature to a level at which gelling or cross-linking is induced, rendering the material non-fluent. Localized heating or cooling can be enhanced by providing a flow of heated or chilled liquid directly onto the treatment site. Thermal control can also be provided, however, using a fluid flow through or into the balloon, or using a partially perforated balloon such that temperature control fluid passes through the balloon into the lumen. Thermal control can also be provided using electrical resistance heating via a wire running along the length of the catheter body in contact with resistive heating elements. This type of heating element can make use of DC or radio frequency (RF) current or external RF or microwave radiation. Other methods of achieving temperature control can also be used, including light-induced heating using an internal optical fiber (naked or lensed). Alternatively, as self-contained fluid flow system, allowing inflow and outflow of fluids to the balloon, actuator or other material applying tip of surface may control polymer flow, molding, cooling, and/or fixation.

Application of Solid Materials

Alternatively the polymers may be delivered as solid materials of various configurations, e.g. rods, spheres, folded sheets, yarns, meshes, twines, ropes, particles, amorphous shapes, flakes, etc. Similarly hydrogel materials may be delivered with the above physical geometries in either the hydrated, partially hydrated or dessicated form. Further defined hydrogel shapes, such as spikes, spheres with wicks and other shapes (e.g., tract+void) may be delivered to the desired location.

The foregoing materials can be mixed with other materials to improve their physiological compatibility. These materials include buffers, physiological salts, conventional thickeners or viscosity modifying agents, fillers such as silica and cellulosics, and other known additives of similar function, depending on the specific tissue to which the material is applied.

Fixing the shape of the polymeric material can be accomplished in several ways, depending on the character of the original polymeric material. A partially polymerized material can be expanded using a balloon after which the conditions are adjusted such that polymerization can be completed, e.g., by increasing the local temperature or providing UV or visible radiation through an optical fiber. A temperature increase might also soften a fully polymerized sleeve to allow expansion and facile reconfiguration and local molding, after which it would "freeze" in the expanded position when the head source is removed. If the polymeric sleeve is a plastic material that permanently deforms upon stretching (e.g., polyethylene, polyethylene terephthalate, nylon or polyvinyl chloride), no special fixation procedure is required.

b. Application of Electronic Devices or Components

The polymeric material or prepolymer can contain integrated electronic devices or components, or in some embodiments, the devices and components can be added during the paving procedure. In some embodiments, the integrated devices and components are repositioned during the paving procedure while the polymeric scaffold is in a fluid or semi-fluid state.

The ePEPS can be used to create paving layers, seals, barriers in arteries, coronary arteries, femoral arteries, iliac arteries, renal arteries, vertebral arteries, mesenteric arteries, vessels, the uterus, prostate, neovessels feeding tumors, felopian tubes, ureter, trachea, bronchi, veins such as the femoral, saphenous, or other major veins, or on any endoluminal surface. The ePEPs procedure can also be applied to endomural spaces or voids or to ectoluminal surfaces.

The integrated electronic components are biocompatible or rendered sufficiently biocompatible by encapsulation in a suitable coating material. In some embodiments the coating material is semi-permeable or permeable to only one or a few chemical agents. This is particularly useful for providing integrated electronic components for chemical sensing. The integrated electronic component is in some embodiments completely self-contained. The integrated electronic component is in some embodiments incorporated into a fluent solution of monomer or prepolymer and is left encapsulated within the polymeric scaffold during the in situ polymerization or solidification. In some embodiments the integrated electronic components are sufficiently flexible and on a sufficiently flexible substrate to make conformal contact with the tissue surface. In some embodiments the flexible electronic device is placed in intimate conformal contact with the tissue surface prior to applying the polymeric scaffold. The polymeric scaffold is then applied and maintains the electronic device in intimate conformal contact with the endoluminal surface. Integrated electronic devices may in some embodiments be placed in contact with the interior cavity of a hollow or tubular organ. In some embodiments this can be accomplished by applying a sufficiently flexible integrated electronic device to the surface of the non-fluent polymeric scaffold or the nearly non-fluent polymeric scaffold.

In some embodiments the polymeric material is applied in a state that is sufficiently non-fluent to support a flexible integrated electronic component while still being sufficiently fluent to allow conformal placement on the endoluminal surface. In some embodiments the material forming the polymeric scaffold may serve as a substrate material for one or more integrated electronic components, optionally that may be transfer printed directly onto the polymer substrate material.

IV. Devices

The terms "device", "implant", and "article" are generally used interchangeably herein.

The ePEPS procedure provides for in situ formation of biologically compatible smart implants capable of altering, retarding, enhancing, or monitoring an organ component, an organ, or a physiological system.

In preferred embodiments, the implant is partially or completely biodegradable or time-limited. The polymeric scaffold, the integrated electronic components or devices, or both are biodegradable or time-limited. The rate of degradation is, in some embodiments, timed to coincide with the useful life of the implant or to coincide with the desired timeframe for use. In some embodiments the rate of degradation is such that implant (or the biodegradable components if the implant is only partially biodegradable) degrades by at least 90% over a period of 2 weeks, 2 months, 6 months, 12 months, or 18 months following implantation. This time period typically coincides with the normal healing process or period of recovery following an injury such as a stroke or implantation of a stent or pacemaker. It may also coincide with the period in which the device is operational, such as the life of the power source.

In some embodiments the implant is flexible, conformable, or both flexible and conformable. In preferred embodiments, the implant, or one or more components of the implant, is capable of making conformal contact with a tissue surface. In preferred embodiments, the tissue surface is an endoluminal surface, although other surfaces can be contacted as well.

A smart biomedical implant contains a polymeric scaffold and one or more integrated electronic devices. In some embodiments the polymeric scaffold supports one or more additional components. The polymeric scaffold is preferably biodegradable. In some cases the integrated electronic devices may be biodegradable. In particularly preferred embodiments both the polymeric scaffold and the integrated electronic device are biodegradable. In some instances the rate of degradation of the polymeric scaffold, of the integrated electronic device, or both, may be adjusted to coincide with the desired useful lifetime of the implant. In some embodiments, the polymeric scaffold contains one or more flexible interconnects, either connecting two integrated electronic device, connecting an integrated electronic device to an additional component, or connecting an integrated electronic device locally to the tissue of the organ or organ component.

In addition to operation, to monitor, deliver, store or actuate the "smart" system may have feedback and logic means to respond to a change in local conditions.

An exemplary smart bioelectric paving device containing one or more polymer paving layers; a modular micro "motherboard"; and a microchip/microcircuit is depicted in FIGS. 10A-C. The device also can accept implant microboards.

A. Placement of Smart Biomedical Implants

The smart biomedical implants described herein are generally placed in the tissue, organ, or organ component in such a manner to maximize the desired outcome, i.e. to maximize the enhancement of organ function or to increase the sensitivity for monitoring organ function. In some embodiments the implant adheres to one or more tissue surfaces. In preferred embodiments the implant is in conformal contact or is partially in conformal contact with an endoluminal tissue.

During the step of positioning the material at the desired location, the location may be accessed by either invasive surgical techniques or by relatively non-invasive techniques such as laparoscopic procedures or percutaneous transluminal procedures. In one embodiment, the step in which the fluent polymeric material is contacted with the tissue surface may be considered as a "molding" procedure in which the fluent polymeric material is molded into substantially conforming contact with the body tissue before cooling into a non-fluent coating on the surface.

B. System Integration

The smart bioelectric paving device may contain one or more sensors and a feedback control circuit. The sensor detects one or more physical properties of its surrounding environment, and provides an output signal of the detected physical property to the control circuit. The control circuit then sends data indicative of the detected physical property to a remote reader with an energy coupler or with a different energy coupler.

The control circuit can be encoded with identifying data before or after implantation. Such data may relate to the sensor, the patient into which the device is implanted or both. The identifying data may also be a unique tag for accessing data stored in a remote data bank, such as a personal computer or a memory device in a remote reader. Hence, even after implantation of the implant with sensor(s), identifying data can be retrieved from control circuit in a non-invasive manner, as can data corresponding to sensed parameter values.

Ultrasonic and optical coupling can be used with a transponder for energizing and providing command signals to the transponder, and for transmitting identifying data, including unique tags, from the transponder to a remote reader. A transponder can include more than one energy coupler, particularly where it is advantageous to energize the sensor with one form of energy, and transmit data using another. Where desirable, a third energy coupler can also receive control commands from an external source using either the same or different forms of energy as those used for energizing the transponder and transmitting data therefrom.

Table 1 describes some exemplary applications of ePEPS. For treating infections, sensors can detect for changes in pH, oxygen levels, muscle tension, temperature, and integrated devices can apply electronic, ultrasonic, enzymatic and/or thermal energy to treat the infection. Muscle contractions can be detected and/or stimulated by integrated electronic devices detecting or applying electrical pulses. This may be useful for detecting, stimulating or regulating cardiac contractions, in the bladder, or in smooth muscles. Sensors can detect changes in mass or generic buildup of specific cells, for example, on a coating layer around an implant or on a smart implant as occurs with restenosis or neointimal thickening or general tissue build-up or fouling, and by applying electric current, heat, or radiation locally via one or more integrated devices can mediate or initiate apoptosis or necrosis locally.

In some embodiments, the devices described herein can be used with pharmaceutical pills or capsules, suppositories, patches, or other drug delivery means. Sensors supported in the polymeric scaffold can monitor transit through the body, rates of drug release or degradation, area of delivery, or even a patient's compliance with a dosing regimen.

TABLE 1

Exemplary BioMedical targets and applications of ePEPS and smart implants.

| Biological Process/Mechanism | Detection/Sensing | Manipulation/Therapy |
|---|---|---|
| Infection | pH change, $O_2$ tension, temperature | Electrosterilization (thermal) |
| Skeletal Muscle contraction | EMG signals | Electrical stimulation/pacing |
| Peristalsis (Smooth muscle) | EMG signals | Electrical stimulation/pacing |
| Cardiac contraction | EMG signals | Electrical stimulation/pacing |
| Bladder contraction | EMG signals | Electrical stimulation/pacing |
| Protein denaturation (therapeutic remodeling) | | Thermal shrinkage - e.g. collagen ligaments |
| Secretion (endocrine and exocrine function) | Nerve conduction | 1. Electrical stimulation of efferent nerves 2. Direct glandular stimulation |
| Cellular/tissue ablation | Generic Mass buildup, specific cell detection | Mediation or activation of apoptosis, anoikis, necrosis via current, heat, ultrasound, UV or other radiation. |
| Cellular (benign or malignant)infiltration/ Inflammation | pH change, specific mediator release, specific cell presence, temperature | Mediation or activation of apoptosis, anoikis, necrosis via current, heat, ultrasound, UV or other radiation. |

C. Smart Stents, Tubes, and Drains

In some embodiments, ePEPS can be used to form smart stents, tubes, or drains in vivo. Stents generally refers to a biomedical implant or structure that adds rigidity, support, or expansion force to a lumen surface or to a prosthesis. Stents are commonly tubular or spring-like support structures, although this need not necessarily be the case. Stents are placed in contact with all or a portion of a lumen wall. As used herein, "tubes" refers generally to any structure having two or more apertures connected by a conduit. In some embodiments, tube refers to an elongated structure having two apertures connected by a conduit.

Stents may range from about 0.5 mm, i.e. for applications in lacrimal ducts or small vessels, to more typical sizes of about 2 mm-4 mm in coronary arteries, about 3 mm-8 mm in peripheral arteries, and about 8 mm-30 mm in large vessels and the aorta. It is understood that smaller and larger dimensions may be fashioned as well for specific applications. Larger sizes may be utilized in aneurysm or in internal cavities like the ventricle of the heart, the inside of the stomach, uterus or peritoneum or thoracic cavity.

The term "drain" refers to often tubular devices used for the removal of fluids such as serum, blood, or bile from a body cavity. Drains have a first end and second end, each having an aperture, with the first end placed within the body cavity and the second end extending outside the body. Smart stents, tubes, and drains produced by ePEPS improve over existing stent technology, can be formed in vivo in a non-invasive or less invasive procedure than existing preformed metal and polymeric stents, and include integrated electronic components providing for non-invasive local monitoring, enhancement, attenuation and/or impact. Incorporated electronics in ePEPS in drains may be utilized to measure flow, fluid accumulation, presence of thrombus or development of infection, for example.

The stents, tubes, and drains contain one or more integrated electronic components providing local monitoring, enhancement, attenuation, and/or impacting of the function of an organ or organ component. The stents, tube, and drains can contain one or more integrated electronic components capable of storing, transmitting, and/or receiving data. The polymeric scaffold forming the stents, tubes, and drains can serve as a controlled release matrix or can contain a controlled release polymer matrix for delivery of one or more therapeutic or diagnostic agents.

The smart stents, tubes, and drains can contain one or more sensing elements capable of detecting infection, i.e. by sensing local changes in temperature, pH, or $O_2$ tension. The smart stents, tubes, and drains can contain one or more integrated electronic components capable of providing an anti-infective effect. An integrated electronic component may impart anti-infective properties by generating a local current or charge in the area around the tissue. An integrated electronic component may impart anti-infective properties by controlling the release of an anti-infective agent. In some embodiments the polymeric scaffold contains one or more reservoirs containing one or more anti-infective agents. In some embodiments the reservoirs have a reservoir cap controlling release of the one or more anti-infective agents. The reservoir caps can be controllably disintegrated or permeabilized by an integrated electronic component, for example by electrothermal ablation of the reservoir cap. The reservoir cap can be a thin metal film, impermeable to the surrounding environment (e.g., body fluids). Suitable reservoir cap materials can include metals such as gold, silver, copper, and zinc. An integrated electronic component having a pair of electrodes in electrical contact with the reservoir cap can be used to apply an electric potential or current, thereby disintegrating the reservoir cap or oxidizing the reservoir cap.

In some embodiments the smart stents, tubes, and drains contain one or more electrodes capable of electrically stimulating the adjacent tissue. Smart stents, tubes, and drains are provided containing two or more electrodes in electrical contact with the adjacent tissue, organ, or organ component. The electrodes are electrically connected to a current generating component and positioned such that a current is capable of being generated in the adjacent tissue, organ, or organ component. In some embodiments the current generating component is a pulse generator, capable of applying an electrical pulse across the electrodes. For example, the current generating component can be an electrical storage device such as a capacitor. The pulse may be used to generate precisely-timed contractions in the adjacent tissue, organ, or organ component. In some embodiments the current generating component produces an AC current. An AC current may promote local healing of damaged tissue or may provide reduction of swelling, inflammation, or pain.

Smart stents, tubes, or drains can contain a controlled release polymer matrix providing delivery of one or more therapeutic, prophylactic, or diagnostic agents. In some embodiments the stents include one or more reservoirs having reservoir caps controlling release of the therapeutic, prophylactic, or diagnostic agents. The reservoir caps can be controllably disintegrated or permeabilized by an integrated electronic component. Examples of therapeutic agents can include anti-thrombogenic agents, anti-proliferative agents, anti-inflammatory agents, analgesics, anesthetic agents, anti-coagulants, vascular cell growth promoters, vascular cell growth inhibitors, cholesterol-lowering agents, and vasodilators.

Smart stents tubes and drains may also contain imaging systems for direct visualization, telemetry systems to offload signals and data and battery and power generating systems as outlined above.

D. Smart Bandages

In some embodiments, ePEPS can be used to form smart bandages. A smart non-fluent biocompatible polymer coating is formed at the site of a wound and molded in vivo to accommodate the necessary size and shape. The polymer coating forms a seal or a semipermeable barrier over the wound. A smart bandage includes one or more integrated electronic component. The integrated electronic components may include one or more sensors to detect the presence of biological fluids, biological agents, genetic material, radiation, medication, oxygen, blood gases, blood cell count, temperature, pulse, or indicia of contamination and/or infection.

The smart bandages can contain one or more sensing elements capable of detecting infection, i.e. by sensing local changes in temperature, pH, or $O_2$ tension. The smart bandages can contain one or more integrated electronic components capable of providing an anti-infective effect. An integrated electronic component may impart anti-infective properties by generating a local current or charge in the area around the wound. An integrated electronic component may impart anti-infective properties by controlling the release of an anti-infective agent. In some embodiments the polymeric scaffold in a smart bandage contains one or more reservoirs containing one or more anti-infective agents. In some embodiments the reservoirs have a reservoir cap controlling release of the one or more anti-infective agents. The reservoir caps can be controllably disintegrated or permeabilized by an integrated electronic component, for example by electrothermal ablation of the reservoir cap. The reservoir cap can be a thin metal film, impermeable to the surrounding environment (e.g., body fluids). Suitable reservoir cap materials can include metals such as gold, silver, copper, and zinc. An integrated electronic component having a pair of electrodes in electrical contact with the reservoir cap can be used to apply an electric potential or current, thereby disintegrating the reservoir cap or oxidizing the reservoir cap.

In some embodiments the smart bandage contains one or more electrodes capable of electrically stimulating the tissue around the wound. Smart bandages are provided containing one or more electrodes in electrical contact with the tissue around the wound. The electrodes are electrically connected to a current generating component and positioned such that a current is capable of being generated in the tissue around the wound. In some embodiments the current generating component produces an AC current. An AC current may promote local healing of damaged tissue or may provide reduction of swelling, inflammation, or pain.

Smart bandages can contain a controlled release polymer matrix providing delivery of one or more therapeutic, prophylactic, or diagnostic agents. In some embodiments the bandages include one or more reservoirs having reservoir caps controlling release of the therapeutic, prophylactic, or diagnostic agents. The reservoir caps can be controllably disintegrated or permeabilized by an integrated electronic component. Therapeutic agents can include agents that promote wound healing or wound hydration; prevent infection, inflammation, pain, or a combination thereof; or prevent or reduce scarring. Examples can include natural or synthetic growth factors, cytokines, or modulators thereof; hydrating agents; antimicrobial agents; cytokines, growth factors, or hormones.

In some embodiments the smart bandage includes one or more sensors for monitoring the moisture level at the site of the wound. In some embodiments smart bandages maintain a moist environment to promote healing by preventing cellular dehydration and encouraging collagen synthesis and angiogenesis. In some embodiments the smart bandage promotes release of one or more hydrating agents or moisturizers. Hydrating agents can include glycerine, sorbitol, polyalkylene glycols such as polyethylene glycol and polypropylene glycol, urea, and combinations thereof. Accumulation of fluid can promote infection. In some embodiments the smart bandage can adjust porosity of the polymeric scaffold to control water vapor transmission and thereby hydration levels at the wound. The water vapor transmission rate can vary dependent upon the type and location of the wound and the healing stage.

In some embodiments, smart bandages may contain active, passive, or a combination thereof of vacuum, negative pressure, dessication, suction or other means to pull fluid, serum, exudate, tissue or other material that has built up, been exuded or otherwise become resident in a wound. The smart bandage system involving ePEPS applies macro- as well as micro-strain to the wound. This removes material as well as applies mechanical forces that facilitate wound healing, including healthy tissue in-migration, proliferation as well as promotion of angiogenesis. This system is an improvement over large bulky wound vac systems.

E. Biodegradable Cardiac Devices

In some embodiments, ePEPS can be used to form cardiac devices such as pacemakers and/or pacemaker leads; defibrillators, rhythm monitoring devices, or cardiac synchronization devices. The cardiac device can be entirely or partially biodegradable. The cardiac devices produced by ePEPS improve over existing cardiac device technology, i.e. existing pacemakers, and can be formed in vivo in a non-invasive or less invasive procedure than existing pre-formed devices. Conventional cardiac devices such as defibrillators and cardiac synchronization devices include one or more leads placed within the atrial or ventricular tissue and connected to a pulse generator exterior to the heart muscle, typically implanted beneath the skin. Surgical procedures to remove the cardiac devices are avoided by providing biodegradable components where the rate of degradation is timed to coincide with the useful life of the implant.

The cardiac devices contain one or more integrated electronic components providing local monitoring, enhancement, attenuation, and/or impacting of the cardiac function. The cardiac devices can contain one or more integrated electronic components capable of storing, transmitting, and/or receiving data. The polymeric scaffold forming the cardiac devices can serve as a controlled release matrix or can contain a controlled release polymer matrix for delivery of one or more therapeutic or diagnostic agents.

In some embodiments the cardiac devices contain one or more electrodes capable of electrically stimulating cardiac function or monitoring cardiac function. The electrodes can be electrically connected to a current generating component and positioned such that a current is capable of being generated in the cardiac tissue. In some embodiments the current generating component is a pulse generator, capable of applying an electrical pulse across the electrodes. For example, the current generating component can be an electrical storage device such as a capacitor. The pulse may be used to generate precisely-timed contractions in the cardiac tissue.

F. Biodegradable Impant Sensors/Monitors

In some embodiments electro-active paving layers may be applied within a body cavity, on a contained tissue surface, on a contained organ surface, or on or in endoluminal or endomural surfaces or spaces for transient monitoring. An example here is in the surgical domain. Following lance and drainage of an intercavitary abcess a bio-electronic paving layer may be applied to monitor the level of serous fluid that accumulates or the remainder of residual infection. This device may record or telemeter data for physician interpretation. The device may be smart with auto-feedback capability, delivering antimicrobial therapy on demand with detection of infection. Further the device may biodegrade, such as degrade at a defined time point, e.g. 2 months post deployment, or degrade upon external activation, determined by the health care team.

EXAMPLES

Example 1: Two Element Bio-Electronic Paving

Thin film electronics (representative integrated circuits, e.g. 1×2 cm) were applied onto polycaprolactone thin film (a series of dimensions utilized for both, i.e. 0.1-1 mm, 2×4 cm). Sandwiched layers were rolled on a mandrel and placed over a balloon dilatation catheter. The composite sandwich of components was placed inside of a tubular structure, e.g. mock blood vessel, isolated porcine vessel, rabbit esophagus, and transiently heated (0-30 sec.) to (50-70° C.) and immediately cooled (4-37° C.)

Results

The endoluminal surface of all tubular structures tested was successfully "paved" with an endoluminal paving layer. The inner surface of the overall tissue polymer construct was smooth and generally circular, the shape dictated by the shape of the dilating balloon. The interface of the paving layer with the underlying tissue was noted to intimately conformal, with >95% of the circumference conformal to the underlying tissue architecture.

Upon examination the paving layer was noted to be a single continuum with admixed electronics and polymer. Electronic elements were noted to be detectable on the surface to which initially applied, i.e. either abluminal or adluminal, yet clearly imbedded and part of the paving article mass.

Example 2: Multi-Element Bio-Electronic Paving

Thin film electronics (representative integrated circuits, e.g. fabricated as small electronic components referred to as "chiplets"—2×2 mm), were applied onto polycaprolactone (PCL) thin film (a series of dimensions utilized for both, i.e. 0.1-1 mm, 2×4 cm). Chiplets were applied onto one (top or bottom) or both sides of the PCL film. Chiplets were adherent via either surface tension, mild applied pressure or tacking with a biocompatible adhesive, e.g. fibrin glue, 50% dextrose or acrylates. The composite of PCL and chiplets were rolled on a mandrel and placed over a balloon dilatation catheter. The composite sandwich of components was placed inside of a tubular structure, e.g. mock blood vessel, isolated porcine vessel, rabbit esophagus, and transiently heated (0-30 sec) to (50-70° C.) and immediately cooled (4-37° C.).

Results

The endoluminal surface of all tubular structures tested was successfully "paved" with an endoluminal paving layer. The inner surface of the overall tissue polymer construct was smooth and generally circular, the shape dictated by the shape of the dilating balloon. The interface of the paving layer with the underlying tissue was noted to intimately conformal, with >95% of the circumference conformal to the underlying tissue architecture. Upon examination the paving layer was noted to be a single continuum with admixed electronics and polymer. Electronic elements were noted to be detectable on the surface to which initially applied, i.e. either abluminal or adluminal, yet clearly imbedded and part of the paving article mass. Individual chiplets were noted to be distributed on the paving layer in alignment consistent with their original placement, yet proportionally reconfigured and redistributed with the molding that occurred with paving, i.e. going from non-fluent to fluent to non-fluent state.

Example 3: Multi-Layer, Multi-Element Bio-Electronic Paving

Thin film electronics (representative integrated circuits, e.g. fabricated as "chiplets"—2×2 mm), were applied between two polycaprolactone (PCL) thin film layers (a series of dimensions utilized for both, i.e. 0.1-1 mm, 2×4 cm). Chiplets were applied onto the bottom surface of one PCL layer and/or the top surface of the second PCL layer. Further in an extension of this experiment chiplets were also applied to the (top or bottom) of either of the PCL film layers. Chiplets were adherent via either surface tension, mild applied pressure or tacking with a biocompatible adhesive, e.g. fibrin glue, 50% dextrose or acrylates. The composite of PCL and chiplets were rolled on a mandrel and placed over a balloon dilatation catheter. The composite sandwich of components was placed inside of a tubular structure—e.g. mock blood vessel, isolated porcine vessel, rabbit esophagus, and transiently heated (0-30 sec) to (50-70° C.) and immediately cooled (4-37° C.).

Results

The endoluminal surface of all tubular structures tested was successfully "paved" with an endoluminal paving layer. The inner surface of the overall tissue polymer construct was smooth and generally circular, the shape dictated by the shape of the dilating balloon. The interface of the paving layer with the underlying tissue was noted to intimately conformal, with >95% of the circumference conformal to the underlying tissue architecture. Upon examination the paving layer was noted to be a single continuum with admixed electronics and polymer.

Electronic elements were noted to be detectable: 1. within the paving article continuum, 2. on the surface to which initially applied, i.e. either abluminal or adluminal, yet clearly imbedded and part of the paving article mass. Individual chiplets were noted to be distributed on the paving layer in alignment consistent with their original placement, yet proportionally reconfigured and redistributed with the molding that occurred with paving, i.e. going from non-fluent to fluent to non-fluent state.

Example 4: Two-element Stretchable Bio-Electronic Paving

Thin film electronics (representative integrated circuits, e.g. fabricated with "stretchable interconnects"—serpentine or "Z"' shaped redundant trace interconnects, overall dimensions—2×2 mm), were applied onto polycaprolactone-polyurethane (PCL/PU) blend (See Ashton et al, "Polymeric endoaortic paving: Mechanical, thermoforming, and degradation properties of polycaprolactone/polyurethane blends for cardiovascular applications," *Acta Biomaterialia*, 7(1), 287-94, (2011)) thin films (a series of dimensions utilized for both, i.e. 0.1-1 mm, 2×4 cm).

The composite of PCL/PU and the electronics were rolled on a mandrel and placed over a balloon dilatation catheter. The catheter utilized had a final inflated diameter (6-20 mm), i.e. significantly larger than the circumference that would develop from simple tacking of the paving layer, i.e. a size that would stretch the paving layer during deployment. The composite of PCL/PU and the electronics was placed inside of a tubular structure, e.g. mock blood vessel, isolated porcine vessel—e.g. iliac or aorta, rabbit esophagus, and transiently heated (0-30 sec) to (50-70° C.) and immediately cooled (4-37° C.).

Results

The endoluminal surface of all tubular structures tested was successfully "paved" with an endoluminal paving layer. The inner surface of the overall tissue polymer construct was smooth and generally circular, the shape dictated by the shape of the dilating balloon. The interface of the paving layer with the underlying tissue was noted to intimately conformal, with >95% of the circumference conformal to the underlying tissue architecture. The paving composite article was noted to be "thinned," i.e. thinner than the original pre-deployment thickness, consistent with stretching of the layer.

Upon examination the paving layer was noted to be a single continuum with admixed electronics and polymer. Electronic elements were noted to be detectable on the surface to which initially applied, i.e. either abluminal or adluminal, yet clearly imbedded and part of the paving article mass.

The electronic elements were noted to be dispersed yet interconnected, with the interconnects now elongated and stretched. Individual electronic elements were noted to be distributed on the paving layer in alignment consistent with their original placement, yet proportionally spaced apart and reconfigured and redistributed with the stretching and molding that occurred with paving, i.e. going from non-fluent to fluent to non-fluent state.

Unless defined otherwise, all technical and scientific terms used herein have the same meanings as commonly understood by one of skill in the art to which the disclosed invention belongs. Those skilled in the art will recognize, or be able to ascertain using no more than routine experimentation, many equivalents to the specific embodiments of the invention described. Such equivalents are encompassed by the following claims.

I claim:

1. A method for making a device for electropolymeric paving, the method comprising:
   (a) selecting a biocompatible polymeric material;
   (b) selecting electronic components useful for sensing or detecting one or more analytes, signals or conditions; storing data from said electronic components, transmitting or generating an output signal; or effecting a therapy or releasing a therapeutic, prophylactic or diagnostic agent, wherein the electronic components are flexible and stretchable; and
   (c) positioning the electronic components in or on the polymeric material, wherein the polymeric material is able to convert from a fluent state to a less fluent state in vivo, by a change in temperature, electrical current, ultrasound, polymerization, or interaction with a biological fluid,
   wherein when the polymeric material is in the fluent state the polymeric material has a sufficient viscosity to support and/or maintain the electronic components in position in or on the polymeric material, and wherein the electronic components retain their alignment in or on the polymeric material when the polymeric material converts from the fluent state to the less fluent state.

2. The method of claim 1, wherein the polymeric material comprises monomers or partially polymerized prepolymers, and wherein the method further comprises (d) polymerizing at the time or delivery the monomers or partially polymerized prepolymers.

3. The method of claim 1, wherein the polymeric material is biodegradable.

4. The method of claim 1, wherein one or more of the electronic components are non-degradable.

5. The method of claim 1, further comprising (d) providing a stent or a continuous, perforated, or helical sleeve.

6. The method of claim 1, wherein the electronic components are selected from the group consisting of sensors, actuators, power storage, and power sources.

7. The method of claim 1, wherein the polymeric material is able to degrade by hydrolysis, oxidation, enzymatic degradation, reductive mechanisms, Norrish type I or type II ester formation, and/or corrosion.

8. The method of claim 1, wherein the electronic components are homogenously distributed in the polymeric material.

9. The method of claim 1, wherein the electronic components are heterogeneously distributed in the polymeric material.

10. The method of claim 1, wherein the electronic components are located on the top, middle or bottom of the polymeric material, or a combination thereof.

11. The method of claim 1, wherein the electronic components are able to sense flow, pressure, pH change, specific analytes, change in mass, or changes in cells or in tissue.

12. The method of claim 1, further comprising (d) providing nested loops to store, interrogate, and/or telemeter data.

13. The method of claim 1, further comprising (d) converting the polymeric material from a fluent state to a less fluent state.

14. The method of claim 13, wherein following step (d), the polymeric material has a sufficient thickness to isolate or reduce the strain on the electronic components.

15. The method of claim 13, wherein following step (d), the polymeric material has a thickness of less than or equal to 300 pm, less than Or equal to 200 pm, or less than or equal to 50 pm.

16. The method of claim 1, wherein in the fluent state, the polymeric material has a suitable viscosity and flow properties to fill uneven surface interstices of a tissue in the body while maintaining a smooth surface.

17. The method of claim 1, wherein the viscosity of the polymeric material in the fluent state ranges from 1 cP to $10^6$ cP at body temperature.

* * * * *